United States Patent
Rivas et al.

(10) Patent No.: US 10,330,643 B2
(45) Date of Patent: Jun. 25, 2019

(54) BAW SENSING AND FILTRATION DEVICE AND RELATED METHODS

(71) Applicant: Qorvo US, Inc., Greensboro, NC (US)

(72) Inventors: Rio Rivas, Bend, OR (US); Vincent K. Gustafson, Chapel Hill, NC (US)

(73) Assignee: QORVO US, INC., Greensboro, NC (US)

( * ) Notice: Subject to any disclaimer, the term of this patent is extended or adjusted under 35 U.S.C. 154(b) by 0 days.

(21) Appl. No.: 15/423,141

(22) Filed: Feb. 2, 2017

(65) Prior Publication Data

US 2017/0227497 A1    Aug. 10, 2017

Related U.S. Application Data

(60) Provisional application No. 62/291,291, filed on Feb. 4, 2016.

(51) Int. Cl.
*H01L 41/113* (2006.01)
*G01N 29/02* (2006.01)
(Continued)

(52) U.S. Cl.
CPC .......... *G01N 29/022* (2013.01); *G01N 29/036* (2013.01); *G01N 29/222* (2013.01);
(Continued)

(58) Field of Classification Search
CPC ............ H01L 41/0805; H01L 41/1132; G01N 29/222; G01N 2291/012; G01N 2291/015;
(Continued)

(56) References Cited

U.S. PATENT DOCUMENTS

| 4,640,756 A | 2/1987 | Wang et al. |
| 5,666,143 A | 9/1997 | Burke et al. |

(Continued)

OTHER PUBLICATIONS

Qorvo US, Inc., "Summary of Sales Activity of Predecessor to Applicant Concerning Tilted C-Axis Aluminum Nitride Products," Unpublished, Jan. 10, 2017, 1 page.

(Continued)

*Primary Examiner* — Robert R Raevis
(74) *Attorney, Agent, or Firm* — Mueting, Raasch & Gebhardt, P.A.

(57) ABSTRACT

A fluidic device incorporating at least one BAW resonator structure (e.g., a biosensing device) and a fluidic passage includes one or more features that provide filtration capability. Certain embodiments include at least one group of pillars extending into the fluidic passage which are arranged between an active region of the at least one BAW resonator structure and at least one fluidic port. Individual pillars are separated from one another by inter-pillar spaces that provide redundant fluid flow paths while preventing passage of obstruction media such as particulate matter, cells, and/or bubbles. Certain embodiments provide porous material arranged in fluid communication with at least one fluidic port and configured to filter contents of fluid supplied thereto. Porous material (e.g., porous membranes) may be provided in a cover structure of a fluidic device or within a filtration cartridge.

14 Claims, 18 Drawing Sheets

(51) Int. Cl.
- *H01L 41/08* (2006.01)
- *G01N 29/22* (2006.01)
- *G01N 29/036* (2006.01)

(52) U.S. Cl.
CPC ...... *H01L 41/0805* (2013.01); *H01L 41/1132* (2013.01); *G01N 2291/012* (2013.01); *G01N 2291/015* (2013.01); *G01N 2291/0255* (2013.01); *G01N 2291/0256* (2013.01); *G01N 2291/0426* (2013.01)

(58) Field of Classification Search
CPC ... G01N 2291/0255; G01N 2291/0256; G01N 2291/0426; G01N 29/022–036; G01N 2291/021–0028; G01N 29/036
USPC ............ 73/64.53, 23.2, 23.34, 24.01, 24.06, 73/31.03, 31.05, 35.06, 61.49, 570, 73/863.21, 863.23; 422/68.1, 69, 83; 435/4–40.52
See application file for complete search history.

(56) References Cited

U.S. PATENT DOCUMENTS

| | | | |
|---|---|---|---|
| 5,734,399 A | 3/1998 | Weber et al. | |
| 6,748,978 B2 | 6/2004 | Pezzuto et al. | |
| 6,814,859 B2 | 11/2004 | Koehler et al. | |
| 7,468,608 B2 | 12/2008 | Feucht et al. | |
| 8,409,875 B2 | 4/2013 | Johal et al. | |
| 2011/0209524 A1* | 9/2011 | Ziglioli | G01N 33/0009 73/23.34 |
| 2017/0108471 A1* | 4/2017 | Sturtevant | G01N 29/228 |

OTHER PUBLICATIONS

Chen, Ying-Chung et al., "The Liquid Sensor Using Thin Film Bulk Acoustic Resonator with C-Axis Tilted AlN Films," Journal of Nanomaterials, vol. 2013, Article ID 245095, 2013, 8 pages.

Corso, Christopher et al., "Development of a Simple Inexpensive Bulk Acoustic Wave (BAW) Nanosensor for Cancer Biomarkers: Detection of Secreted Sonic Hedgehog from Prostate Cancer Cells," Abstract #8866, Winship Cancer Institute, Emory University, Georgia Institute of Technology, Oct. 2012, 1 page.

Dey, P.K. et al., "Microstructuring of SU-8 Resist for MEMS and Bio-Applications," International Journal on Smart Sensing and Intelligent Systems, vol. 3, No. 1, Mar. 2010, pp. 118-129.

Lee, Chia-Yen et al., "Microfluidic Mixing: A Review," International Journal of Molecular Sciences, vol. 12, May 18, 2011, pp. 3263-3287.

Link, Mathias, "Study and realization of shear wave mode solidly mounted film bulk acoustic resonators (FBAR) made of c-axis inclined zinc oxide (ZnO) thin films: application as gravimetric sensors in liquid environments," Université Henri Poincaré—Nancy I, Thesis, Sep. 14, 2006, 225 pages.

Milyutin, Evgeny, "Theoretical and Experimental Study of Piezoelectric Modulated AlN Thin Films for Shear Mode BAW Resonators," EPFL, Thesis No. 5113, Nov. 4, 2011, 109 pages.

Munir, Farasat, "A Fast, Scalable Acoustic Resonator-Based Biosensor Array System for Simultaneous Detection of Multiple Biomarkers," Thesis, Georgia Institute of Technology, Dec. 2012, 160 pages.

Nirschl, Martin et al., "CMOS-Integrated Film Bulk Acoustic Resonators for Label-Free Biosensing," Sensors, vol. 10, No. 5, Apr. 27, 2010, pp. 4180-4193.

Ramakrishnan, N. et al., "Resonant Frequency Characteristics of a SAW Device Attached to Resonating Micropillars," Sensors, vol. 12, No. 4, Mar. 23, 2012, pp. 3789-3797.

Wangler, N. et al., "High-resolution permanent photoresist laminate TMMF for sealed microfluidic structures in biological applications," Journal of Micromechanics and Microengineering, vol. 21, Aug. 4, 2011, IOP Publishing, 9 pages.

Yu, Hongyu et al., "Ultra Temperature-Stable Bulk-Acoustic-Wave Resonators with $SiO_2$ Compensation Layer," IEEE Transactions on Ultrasonics, Ferroelectrics, and Frequency Control, vol. 54, No. 10, Oct. 2007, pp. 2102-2109.

Zhou, Yan et al., "Interfacial Structures and Properties of Organic Materials for Biosensors: An Overview," Sensors, vol. 12, Nov. 6, 2012, pp. 15036-15062.

\* cited by examiner

BAW SENSING AND FILTRATION DEVICE AND RELATED METHODS

STATEMENT OF RELATED APPLICATIONS

This application claims the benefit of provisional patent application Ser. No. 62/291,291, filed Feb. 4, 2016, the disclosure of which is hereby incorporated herein by reference in its entirety.

TECHNICAL FIELD

The present disclosure relates to fluidic devices incorporating acoustic resonators, including fluidic devices and related systems suitable for biosensing or biochemical sensing applications.

BACKGROUND

A biosensor (or biological sensor) is an analytical device including a biological element and a transducer that converts a biological response into an electrical signal. Certain biosensors involve a selective biochemical reaction between a specific binding material (e.g., an antibody, a receptor, a ligand, etc.) and a target species (e.g., molecule, protein, DNA, virus, bacteria, etc.), and the product of this highly specific reaction is converted into a measurable quantity by a transducer. Other sensors may utilize a non-specific binding material capable of binding multiple types or classes of molecules or other moieties that may be present in a sample, such as may be useful in chemical sensing applications. The term "functionalization material" may be used herein to generally relate to both specific and non-specific binding materials. Transduction methods may be based on various principles, such as electrochemical, optical, electrical, acoustic, and so on. Among these, acoustic transduction offers a number of potential advantages, such as being real time, label-free, and low cost, as well as exhibiting high sensitivity.

An acoustic wave device employs an acoustic wave that propagates through or on the surface of a piezoelectric material, whereby any changes to the characteristics of the propagation path affect the velocity and/or amplitude of the wave. Presence of functionalization material embodied in a specific binding material along an active region of an acoustic wave device permits a specific analyte to be bound to the specific binding material, thereby altering the mass being vibrated by the acoustic wave and altering the wave propagation characteristics (e.g., velocity, thereby altering resonance frequency). Changes in velocity can be monitored by measuring the frequency, amplitude-magnitude, or phase characteristics of the acoustic wave device, and can be correlated to a physical quantity being measured.

In the case of a piezoelectric crystal resonator, an acoustic wave may embody either a bulk acoustic wave (BAW) propagating through the interior of a piezoelectric material, or a surface acoustic wave (SAW) propagating on the surface of the piezoelectric material. SAW devices involve transduction of acoustic waves (commonly including two-dimensional Rayleigh waves) utilizing interdigital transducers along the surface of a piezoelectric material, with the waves being confined to a penetration depth of about one wavelength. BAW devices typically involve transduction of an acoustic wave using electrodes arranged on opposing top and bottom surfaces of a piezoelectric material. In a BAW device, three wave modes can propagate, namely, one longitudinal mode (embodying longitudinal waves, also called compressional/extensional waves), and two shear modes (embodying shear waves, also called transverse waves), with longitudinal and shear modes respectively identifying vibrations where particle motion is parallel to or perpendicular to the direction of wave propagation. The longitudinal mode is characterized by compression and elongation in the direction of the propagation, whereas the shear modes consist of motion perpendicular to the direction of propagation with no local change of volume. Longitudinal and shear modes propagate at different velocities. In practice, these modes are not necessarily pure modes, as the particle vibration, or polarization, is neither purely parallel nor purely perpendicular to the propagation direction. The propagation characteristics of the respective modes depend on the material properties and propagation direction respective to the c-axis orientations. The ability to create shear displacements is beneficial for operation of acoustic wave devices with fluids (e.g., liquids) because shear waves do not impart significant energy into fluids.

Certain piezoelectric thin films are capable of exciting both longitudinal and shear mode resonance, such as hexagonal crystal structure piezoelectric materials including (but not limited to) aluminum nitride (AlN) and zinc oxide (ZnO). To excite a wave including a shear mode using a piezoelectric material arranged between electrodes, a polarization axis in a piezoelectric thin film must generally be non-perpendicular to (e.g., tilted relative to) the film plane. In biological sensing applications involving liquid media, the shear component of the resonator is used. In such applications, piezoelectric material may be grown with a c-axis orientation distribution that is non-perpendicular relative to a face of an underlying substrate to enable a BAW resonator structure to exhibit a dominant shear response upon application of an alternating current signal across electrodes thereof.

Typically, BAW devices are fabricated by micro-electro-mechanical systems (MEMS) fabrication techniques owing to the need to provide microscale features suitable for facilitating high frequency operation. In the context of biosensors, functionalization materials (e.g., specific binding materials; also known as bioactive probes or agents) may be deposited on sensor surfaces by microarray spotting (also known as microarray printing) using a microarray spotting needle. Functionalization materials providing non-specific binding utility (e.g., permitting binding of multiple types or species of molecules) may also be used in certain contexts, such as chemical sensing.

Sensing devices incorporating BAW resonator structures and intended for use with fluids may define fluidic passages configured to direct fluid over an active region. The small dimensions associated with fluidic passages of these devices may make such passages susceptible to occlusion or blockage, such as with particulate material, cells, and/or bubbles (which may be collectively referred to herein as "obstruction media"), wherein complete blockage of a fluidic passage (e.g., a channel, a chamber, or the like) may render a fluidic device inoperable. Additionally, it may be challenging to detect certain types of analytes that are present in low concentration and/or exhibit low rates of binding to functionalization material.

Accordingly, there is a need for devices incorporating bulk acoustic wave resonator structures suitable for operation in the presence of liquid for biosensing or biochemical sensing applications that overcome limitations associated with conventional devices.

SUMMARY

The present disclosure provides fluidic devices incorporating BAW resonator structures with one or more features that provide filtration capability. A cover structure and a wall structure are arranged over a base structure incorporating at least one BAW resonator structure, with first and second fluidic ports providing fluid communication with a fluidic passage containing an active region of the BAW resonator structure. In certain embodiments, at least one plurality of pillars extending into the fluidic passage are arranged between the active region and one or more of the first fluidic port or the second fluidic port, with individual pillars being separated from one another by inter-pillar spaces that enable passage of fluid but may prevent passage of items such as particulate matter, cells, and/or bubbles. In other embodiments, a porous material may be arranged in fluid communication with at least one fluidic port (e.g., the first fluidic port) and configured to filter contents of a fluid supplied to the at least one fluidic port. One example of a desirable porous material is a porous membrane. In certain embodiments, porous material may be arranged in or on a cover structure that defines a fluidic passage; alternatively, a porous material may be arranged upstream of a fluidic port and/or cover structure, such as within a filtration cartridge that is distinct and separable from the cover structure. Methods for fabricating a fluidic device as disclosed herein, as well as methods for biological or chemical sensing using such a fluidic device, are further provided.

In one aspect, a fluidic device includes: a base structure comprising: (i) a substrate; and (ii) at least one bulk acoustic wave resonator structure supported by the substrate, the at least one bulk acoustic wave resonator structure including a piezoelectric material, a top side electrode arranged over a portion of the piezoelectric material, and a bottom side electrode arranged below at least a portion of the piezoelectric material, wherein a portion of the piezoelectric material is arranged between the top side electrode and the bottom side electrode to form an active region; a wall structure arranged over at least a portion of the base structure and defining lateral boundaries of a fluidic passage that is arranged to receive a fluid and contains the active region; a cover structure arranged over the wall structure and defining an upper boundary of the fluidic passage; a first fluidic port arranged in fluid communication with the fluidic passage upstream of the active region; a second fluidic port arranged in fluid communication with the fluidic passage downstream of the active region; and a plurality of upstream pillars extending into the fluidic passage and being arranged between the first fluidic port and the active region, wherein each upstream pillar of the plurality of upstream pillars comprises a height that is at least about 50% of an average height of the fluidic passage upstream of the active region, and adjacent upstream pillars of the plurality of upstream pillars are spaced apart from one another by inter-pillar spaces that enable passage of fluid between the first fluidic port and a portion of the fluidic passage that contains the active region.

In certain embodiments, the plurality of upstream pillars extends upward from the base structure. In certain embodiments, the plurality of upstream pillars extends downward from the cover structure.

In certain embodiments, each upstream pillar of the plurality of upstream pillars comprises a height that is at least about 90% of the average height of the fluidic passage upstream of the active region.

In certain embodiments, the fluidic device further includes a plurality of downstream pillars extending into the fluidic passage and being arranged between the second fluidic port and the active region, wherein each downstream pillar of the plurality of downstream pillars comprises a height that is at least about 50% of an average height of the fluidic passage downstream of the active region, and adjacent downstream pillars of the plurality of downstream pillars are spaced apart from one another by inter-pillar spaces that enable passage of fluid between (i) the portion of the fluidic passage that contains the active region and (ii) the second fluidic port.

In certain embodiments, the plurality of upstream pillars comprises a first group of upstream pillars including a first average inter-pillar spacing distance, and a second group of upstream pillars including a second average inter-pillar spacing distance, wherein the first average inter-pillar spacing distance is greater than the second average inter-pillar spacing distance, and the first group of upstream pillars is arranged between the first fluidic port and the second group of upstream pillars.

In certain embodiments, the fluidic device further includes a plurality of downstream pillars extending into the fluidic passage and being arranged between the second fluidic port and the active region, wherein each downstream pillar of the plurality of downstream pillars comprises a height that is at least about 50% of an average height of the fluidic passage downstream of the active region, and the plurality of downstream pillars includes at least one group of downstream pillars with an inter-pillar spacing distance that is less than the first average inter-pillar spacing distance.

In certain embodiments, the plurality of upstream pillars comprises at least one of a photosensitive material, photoresist, or epoxy.

In certain embodiments, the piezoelectric material comprises a c-axis having an orientation distribution that is predominantly non-parallel to normal of a face of the substrate.

In certain embodiments, the fluidic passage comprises an upstream segment and an intermediate segment arranged downstream of the upstream segment; the plurality of upstream pillars is arranged within the upstream segment; the intermediate segment contains the active region; and the upstream segment comprises a greater cross-sectional area than the intermediate segment.

In certain embodiments, the fluidic device further includes at least one functionalization material arranged over at least a portion of the active region.

In certain embodiments, a method for biological or chemical sensing includes: supplying a fluid containing an analyte into the fluidic passage of the fluidic device as disclosed herein, wherein said supplying is configured to cause at least a portion of the fluid to pass through the inter-pillar spaces and to cause at least some of the analyte to bind to at least one functionalization material; inducing a bulk acoustic wave in the active region; and sensing a change in at least one of an amplitude-magnitude property, a frequency property, or a phase property of the at least one bulk acoustic wave resonator structure to indicate at least one of presence or quantity of target species bound to the at least one functionalization material.

In another aspect, a fluidic device includes: a base structure comprising: (i) a substrate; and (ii) at least one bulk acoustic wave resonator structure supported by the substrate, the at least one bulk acoustic wave resonator structure including a piezoelectric material, a top side electrode arranged over a portion of the piezoelectric material, and a bottom side electrode arranged below at least a portion of the piezoelectric material, wherein a portion of the piezoelectric material is arranged between the top side electrode and the bottom side electrode to form an active region; a wall structure arranged over at least a portion of the base structure and defining lateral boundaries of a fluidic passage that is arranged to receive a fluid and contains the active region; a cover structure arranged over the wall structure and defining an upper boundary of the fluidic passage; a first fluidic port arranged in fluid communication with the fluidic passage upstream of the active region; a second fluidic port arranged in fluid communication with the fluidic passage downstream of the active region; and a porous material in fluid communication with the first fluidic port and configured to filter contents of fluid supplied to the first fluidic port.

In certain embodiments, the porous material comprises a porous membrane. In certain embodiments, the porous material is arranged in or on the cover structure. In certain embodiments, the porous material is arranged upstream of the cover structure. In certain embodiments, the porous material is arranged in a filtration cartridge that is distinct and separable from the cover structure.

In certain embodiments, the piezoelectric material comprises a c-axis having an orientation distribution that is predominantly non-parallel to normal of a face of the substrate.

In certain embodiments, the fluidic device further includes at least one functionalization material arranged over at least a portion of the active region.

In certain embodiments, a method for biological or chemical sensing includes: supplying a fluid containing an analyte into the fluidic passage of the fluidic device as disclosed herein, wherein said supplying is configured to cause at least a portion of the fluid to pass through the porous material and to cause at least some of the analyte to bind to the at least one functionalization material; inducing a bulk acoustic wave in the active region; and sensing a change in at least one of an amplitude-magnitude property, a frequency property, or a phase property of the at least one bulk acoustic wave resonator structure to indicate at least one of presence or quantity of target species bound to the at least one functionalization material.

In another aspect, any one or more aspects or features of one or more embodiments may be combined with aspects or features of one or more other embodiments for additional advantage, unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosure, and together with the description serve to explain the principles of the disclosure.

DETAILED DESCRIPTION

Figure 1:
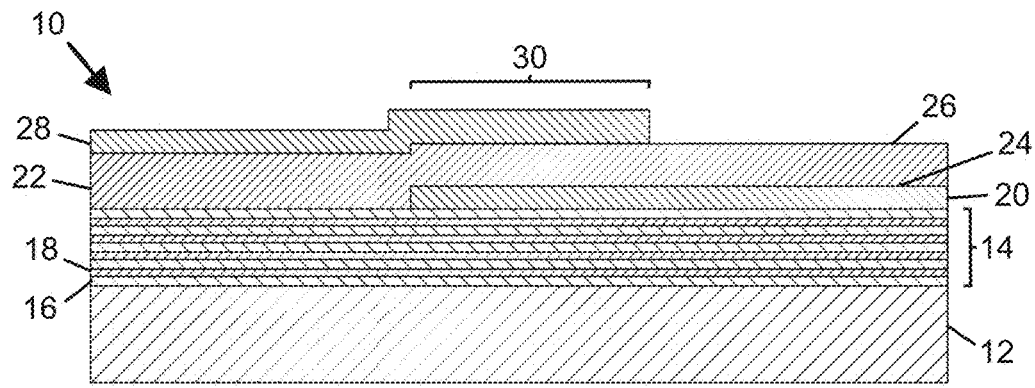
FIG. 1 is a schematic cross-sectional view of a portion of a bulk acoustic wave (BAW) MEMS resonator device usable for fabricating fluidic devices according to embodiments disclosed herein, including an active region with a piezoelectric material arranged between overlapping portions of a top side electrode and a bottom side electrode.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It should be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It should also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It should be understood that, although the terms "upper," "lower," "bottom," "intermediate," "middle," "top," and the like may be used herein to describe various elements, these elements should not be limited by these terms. These terms are only used to distinguish one element from another. For example, a first element could be termed an "upper" element and, similarly, a second element could be termed an "upper" element depending on the relative orientations of these elements, without departing from the scope of the present disclosure.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having meanings that are consistent with their meanings in the context of this specification and the relevant art and will not be interpreted in an idealized or overly formal sense unless expressly so defined herein.

The present disclosure provides fluidic devices incorporating BAW resonator structures with one or more features that provide filtration capability. A cover structure and a wall structure are arranged over a base structure incorporating at least one BAW resonator structure, with first and second fluidic ports providing fluid communication with a fluidic passage containing an active region of the BAW resonator structure. In certain embodiments, at least one plurality of pillars extending into the fluidic passage are arranged between the active region and one or more of the first fluidic port and the second fluidic port, with individual pillars being separated from one another by inter-pillar spaces that enable passage of fluid but may prevent passage of items such as particulate matter, cells, and/or bubbles. In other embodiments, a porous material may be arranged in fluid communication with at least one fluidic port (e.g., the first fluidic port) and port and configured to filter contents of a fluid supplied to the at least one fluidic port. Methods for fabricating a fluidic device as disclosed herein, as well as methods for biological or chemical sensing using such a fluidic device, are further provided.

In certain embodiments, a BAW resonator structure comprises a hexagonal crystal structure piezoelectric material (e.g., aluminum nitride or zinc oxide) that includes a c-axis having an orientation distribution that is non-parallel (and also non-perpendicular) to normal of a face of a substrate over which the piezoelectric material is formed, thereby providing a quasi-shear mode acoustic resonator. Under appropriate conditions, presence of a c-axis having an orientation distribution that is predominantly non-parallel to normal of a face of a substrate enables a BAW resonator structure to be configured to exhibit a dominant shear response upon application of an alternating current signal across a top side electrode and a bottom side electrode. Methods for forming hexagonal crystal structure piezoelectric materials including a c-axis having an orientation distribution that is predominantly non-parallel to normal of a face of a substrate are disclosed in U.S. patent application Ser. No. 15/293,063 filed on Oct. 13, 2016, with the foregoing application hereby being incorporated by reference herein. Additional methods for forming piezoelectric material having an inclined c-axis orientation are disclosed in U.S. Pat. No. 4,640,756 issued on Feb. 3, 1987, with the foregoing patent hereby being incorporated by reference herein.

Before describing fluidic devices incorporating BAW resonator structures with features that provide filtration capability, exemplary bulk acoustic wave MEMS resonator devices, associated layers useful for providing biochemical sensing utility, and fluidic devices incorporating MEMS resonator devices will be introduced.

Micro-electrical-mechanical system (MEMS) resonator devices according to certain embodiments include a substrate, a BAW resonator structure arranged over at least a portion of the substrate, and a functionalization material arranged over at least a portion of an active region of the BAW resonator structure. Various layers may be arranged between the functionalization material and a top side electrode (which is coincident with the active region of the BAW resonator structure), such as: a hermeticity layer (e.g., to protect the top side electrode from corrosion in a liquid environment), an interface layer, and/or a self-assembled monolayer (SAM), with the interface layer and/or the SAM being useful to facilitate attachment of at least one overlying material layer, ultimately including functionalization material. In certain embodiments, the interface layer facilitates attachment of an overlying SAM, and the SAM facilitates attachment of an overlying functionalization material. In certain embodiments, multiple functionalization materials may be provided.

FIG. 1 is a schematic cross-sectional view of a portion of a bulk acoustic wave (BAW) MEMS resonator device 10 useable for fabricating fluidic devices according to at least certain embodiments disclosed herein. The resonator device 10 includes a substrate 12 (e.g., typically silicon or another semiconductor material), an acoustic reflector 14 arranged over the substrate 12, a piezoelectric material 22, and bottom and top side electrodes 20, 28. The bottom side electrode 20 is arranged along a portion of a lower surface 24 of the piezoelectric material 22 (between the acoustic reflector 14 and the piezoelectric material 22), and the top side electrode 28 is arranged along a portion of an upper surface 26 of the piezoelectric material 22. An area in which the piezoelectric material 22 is arranged between overlapping portions of the top side electrode 28 and the bottom side electrode 20 is considered an active region 30 of the resonator device 10. The acoustic reflector 14 serves to reflect acoustic waves and therefore reduce or avoid their dissipation in the substrate 12. In certain embodiments, the acoustic reflector 14 includes alternating thin layers 16, 18 of materials (e.g., silicon oxicarbide [SiOC], silicon nitride [$Si_3N_4$], silicon dioxide [$SiO_2$], aluminum nitride [AlN], tungsten [W], and molybdenum [Mo]) having different acoustic impedance values, optionally embodied in a quarter-wave Bragg mirror, deposited over the substrate 12. In certain embodiments, other types of acoustic reflectors may be used. Steps for forming the resonator device 10 may include depositing the acoustic reflector 14 over the substrate 12, followed by deposition of the bottom side electrode 20, followed by growth (e.g., via sputtering or other appropriate methods) of the piezoelectric material 22, followed by deposition of the top side electrode 28. In certain embodiments, the piezoelectric material 22 comprises a hexagonal crystal structure piezoelectric material (e.g., aluminum nitride or zinc oxide) that includes a c-axis having an orientation distribution that is predominantly non-parallel to (and may also be non-perpendicular to) normal of a face of the substrate 12.

The bulk acoustic wave MEMS resonator device 10 shown in FIG. 1 lacks any layers (e.g., including functionalization material) overlying the active region 30 that would permit the resonator device 10 to be used as a biochemical sensor. If desired, at least portions of the resonator device 10 shown in FIG. 1 (e.g., including the active region 30) may be overlaid with various layers, such as one or more of: a hermeticity layer, an interface layer, a self-assembled monolayer (SAM), and/or a functionalization material (which may include specific binding material or non-specific binding material), as shown in FIG. 2.

Figure 2:
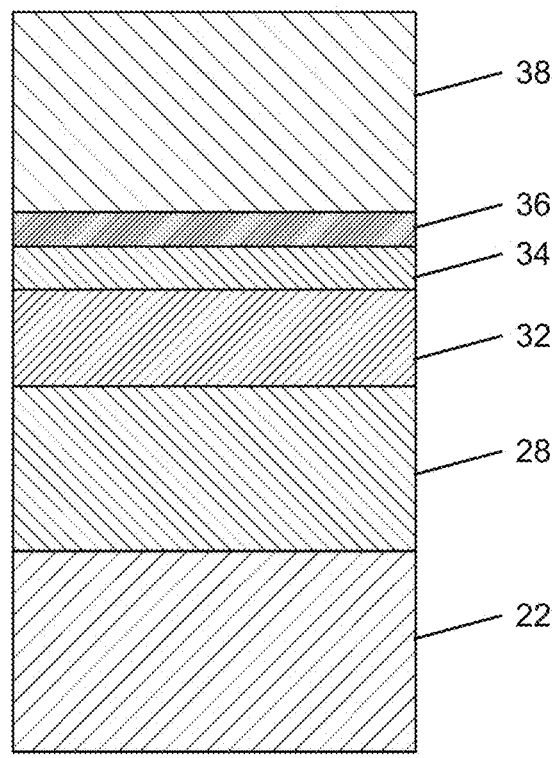
FIG. 2 is a schematic cross-sectional view of an upper portion of a BAW MEMS resonator device including a piezoelectric material and a top side electrode overlaid with a hermeticity layer, an interface layer, a self-assembled monolayer, and a functionalization (e.g., specific binding) material.

FIG. 2 is a schematic cross-sectional view of an upper portion of a BAW MEMS resonator device including a piezoelectric material 22 and a top side electrode 28 overlaid with a hermeticity layer 32, an interface layer 34, a self-assembled monolayer (SAM) 36, and a functionalization (e.g., specific binding) material 38. In certain embodiments, one or more blocking materials (not shown) may be applied during fabrication, such as over portions of the interface layer 34 to prevent localized attachment of one or more subsequently deposited layers, or (if applied over selected regions of the SAM 36 or functionalization material 38) to prevent analyte capture in regions not overlying an active region of the BAW MEMS resonator device.

In certain embodiments, photolithography may be used to promote patterning of interface material or blocking material over portions of a MEMS resonator device. Photolithography involves use of light to transfer a geometric pattern from a photomask to a light-sensitive chemical photoresist on a substrate and is a process well known to those of ordinary skill in the semiconductor fabrication art. Typical steps employed in photolithography include wafer cleaning, photoresist application (involving either positive or negative photoresist), mask alignment, and exposure and development. After features are defined in photoresist on a desired surface, an interface layer may be patterned by etching in one or more gaps in a photoresist layer, and the photoresist layer may be subsequently removed (e.g., by using a liquid photoresist stripper, by ashing via application of an oxygen-containing plasma, or another removal process).

In certain embodiments, an interface layer (e.g., arrangeable between a top side electrode and a SAM) includes a hydroxylated oxide surface suitable for formation of an organosilane SAM. A preferred interface layer material including a hydroxylated oxide surface is silicon dioxide [$SiO_2$]. Alternative materials incorporating hydroxylated oxide surfaces for forming interface layers include titanium dioxide [$TiO_2$], tantalum pentoxide [$Ta_2O_5$], hafnium oxide [$HfO_2$], or aluminum oxide [$Al_2O_3$]. Other alternative materials incorporating hydroxylated oxide surfaces will be known to those skilled in the art, and these alternatives are considered to be within the scope of the present disclosure.

In other embodiments, an interface layer (e.g., arrangeable between a top side electrode and a SAM), or at least one electrode that is devoid of an overlying interface layer, includes gold or another noble metal (e.g., ruthenium, rhodium, palladium, osmium, iridium, platinum, or silver) suitable for receiving a thiol-based SAM that may be overlaid with functionalization material.

In certain embodiments incorporating electrode materials subject to corrosion, a hermeticity layer may be applied between a top side electrode and an interface layer. A hermeticity layer may be unnecessary when noble metals (e.g., gold, platinum, etc.) are used for top side electrodes. If provided, a hermeticity layer preferably includes a dielectric material with a low water vapor transmission rate (e.g., no greater than 0.1 $g/m^2/day$). Following deposition of a hermeticity layer and an interface layer, a SAM may be formed over the interface layer, with the SAM including an organosilane material in certain embodiments. The hermeticity layer protects a reactive electrode material (e.g., aluminum or aluminum alloy) from attack in corrosive liquid environments, and the interface layer facilitates proper chemical binding of the SAM.

In certain embodiments, a hermeticity layer and/or an interface layer may be applied via one or more deposition processes such as atomic layer deposition (ALD), chemical vapor deposition (CVD), or physical vapor deposition (PVD). Of the foregoing processes, ALD is preferred for deposition of at least the hermeticity layer (and may also be preferable for deposition of the interface layer) due to its ability to provide excellent conformal coating with good step coverage over device features so as to provide layer structures that are free of pinholes. Moreover, ALD is capable of forming uniformly thin layers that provide relatively little damping of acoustic vibrations that would otherwise result in degraded device performance. Adequacy of coverage is important for a hermeticity layer (if present) to avoid corrosion of the underlying electrode. If ALD is used for deposition of a hermeticity layer, then in certain embodiments a hermeticity layer may include a thickness in a range of from about 10 nm to about 25 nm. In certain embodiments, hermeticity layer thickness is about 15 nm, or from about 12 nm to about 18 nm. Conversely, if another process such as chemical vapor deposition is used, then a hermeticity layer may include a thickness in a range of from about 80 nm to about 150 nm or more, or in a range of from about 80 nm to about 120 nm. Considering both of the foregoing processes, hermeticity layer thicknesses may range from about 5 nm to about 150 nm. If ALD is used for deposition of an interface layer, then an interface layer may include a thickness in a range of from about 5 nm to about 15 nm. In certain embodiments, an interface layer may include a thickness of about 10 nm, or in a range of from about 8 nm to about 12 nm. Other interface layer thickness ranges and/or deposition techniques other than ALD may be used in certain embodiments. In certain embodiments, a hermeticity layer and an interface layer may be sequentially applied in a vacuum environment, thereby promoting a high-quality interface between the two layers.

If provided, a hermeticity layer may include an oxide, a nitride, or an oxynitride material serving as a dielectric material and having a low water vapor transmission rate (e.g., no greater than 0.1 $g/m^2/day$) according to certain embodiments. In certain embodiments, a hermeticity layer includes at least one of aluminum oxide [$Al_2O_3$] or silicon nitride [SiN]. In certain embodiments, an interface layer includes at least one of $SiO_2$, $TiO_2$, or $Ta_2O_5$. In certain embodiments, multiple materials may be combined in a single hermeticity layer, and/or a hermeticity layer may include multiple sublayers of different materials. Preferably, a hermeticity layer is further selected to promote compatibility with an underlying reactive metal (e.g., aluminum or aluminum alloy) electrode structure of an acoustic resonator structure. Although aluminum or aluminum alloys are frequently used as electrode materials in BAW resonator structures, various transition and post-transition metals can be used for such electrodes.

Following deposition of an interface layer (optionally arranged over an underlying hermeticity layer), a SAM is preferably formed over the interface layer. SAMs are typically formed by exposure of a solid surface to amphiphilic molecules with chemical groups that exhibit strong affinities for the solid surface. When an interface layer comprising a hydroxylated oxide surface is used, then organosilane SAMs are particularly preferred for attachment to the hydroxylated oxide surface. Organosilane SAMs promote surface bonding through silicon-oxygen (Si—O) bonds. More specifically, organosilane molecules include a hydrolytically sensitive group and an organic group and are therefore useful for coupling inorganic materials to organic polymers. An organosilane SAM may be formed by exposing a hydroxylated oxide surface to an organosilane material in the presence of trace amounts of water to form intermediate silanol groups. These groups then react with free hydroxyl groups on the hydroxylated oxide surface to covalently immobilize the organosilane. Examples of possible organosilane-based SAMs that are compatible with interface layers incorporating hydroxylated oxide surfaces include 3-glycidoxypropyltrimethoxysilane (GPTMS), 3-mercaptopropyltrimethoxysilane (MPTMS), 3-aminopropyltrimethoxysilane (APTMS), and octadecyltrimethoxysilane (OTMS), including their ethoxy- and chloro-variants. Additional silanes that may be used for SAMs include poly(ethylene glycol) (PEG) conjugated variants. Those skilled in the art will recognize that other alternatives exist, and these alternatives are considered to be within the scope of the present disclosure. An exemplary SAM may include a thickness in a range of at least 0.5 nm or more. Preferably, a SAM readily binds to the locally patterned interface layer but does not readily bind to other adjacent material layers (e.g., a hermeticity layer, a piezoelectric material, and/or a blocking material layer).

When an electrode and/or interface layer comprising gold or another noble metal is used, then thiol-based (e.g., alkanethiol-based) SAMs may be used. Alkanethiols are molecules with an S—H head group, a tail group, and a back bone comprising an alkyl chain. Thiols may be used on noble metal interface layers due to the strong affinity of sulfur for these metals. Examples of thiol-based SAMs that may be used include, but are not limited to, 1-dodecanethiol (DDT), 11-mercaptoundecanoic acid (MUA), and hydroxyl-terminated (hexaethylene glycol) undecanethiol (1-UDT). These thiols contain the same backbone, but different end groups—namely, methyl ($CH_3$), carboxyl (COOH), and hydroxyl-terminated hexaethylene glycol (HO—($CH_2CH_2O)_6$) for DDT, MUA, and 1-UDT, respectively. In certain embodiments, SAMs may be formed by incubating gold surfaces in thiol solutions using a suitable solvent, such as anhydrous ethanol.

Following formation of a SAM, the SAM may be biologically functionalized, such as by receiving at least one functionalization (e.g., specific binding) material. In certain embodiments, specific binding materials may be applied on or over a SAM using a microarray spotting needle or other suitable methods. In certain embodiments, an interface layer may be patterned (e.g., using photolithographic masking and selective etching for defining the interface layer) with a high dimensional tolerance over only a portion of a BAW resonator structure (which includes a substrate), a SAM may be applied over the interface layer, and a subsequently applied specific binding material may be attached only to the SAM. In certain embodiments, patterning of an interface layer may provide a higher dimensional tolerance for positioning of the specific binding material than could be attained by microarray spotting alone. Examples of specific binding materials include, but are not limited to, antibodies, receptors, ligands, and the like. A specific binding material is preferably configured to receive a predefined target species (e.g., molecule, protein, DNA, virus, bacteria, etc.). A functionalization material including specific binding material may include a thickness in a range of from about 5 nm to about 1000 nm, or from about 5 nm to about 500 nm. In certain embodiments, an array of different specific binding materials may be provided over different active regions of a multi-resonator structure (i.e., one or more resonator structures including multiple active regions), optionally in combination with one or more active regions that are devoid of specific binding materials to serve as comparison (or "reference") regions. In certain embodiments, a functionalization (e.g., bio-functionalization) material may provide non-specific binding utility.

In certain embodiments, a fluidic device may include multiple bulk acoustic wave (BAW) MEMS resonator structures as disclosed herein and a fluidic passage arranged to conduct a liquid to contact at least one functionalization (e.g., specific binding) material arranged over at least one active region of the BAW MEMS resonator structures. Such a device may be microfluidic in scale, and may comprise at least one microfluidic passage (e.g., having at least one dimension, such as height and/or width, of no greater than about 500 microns, or about 250 microns, or about 100 microns). For example, following fabrication of bulk acoustic wave MEMS resonator structures and deposition of a SAM over portions thereof (optionally preceded by deposition of a hermeticity layer and/or an interface layer), a microfluidic device may be fabricated by forming one or more walls defining lateral boundaries of a microfluidic passage over a first bulk acoustic wave MEMS resonator structure with an active region thereof arranged along a bottom surface of the microfluidic passage, and then enclosing the microfluidic passage using a cover or cap layer that may define fluidic ports (e.g., openings) enabling fluid communication with the microfluidic passage. In certain embodiments, functionalization (e.g., specific binding) material may be pre-applied to the active region of a bulk acoustic wave MEMS resonator structure before formation of the microfluidic passage; in other embodiments, functionalization material may be applied over an active region of a bulk acoustic wave resonator structure following formation of the microfluidic passage.

In certain embodiments, a chemical or biological blocking material may be applied over a portion of a SAM to prevent attachment of a functionalization (e.g., specific binding) material over one or more selected regions of a BAW resonator structure (e.g., one or more regions apart from an active region). The proper choice of a chemical or biological blocking material (e.g., blocking buffer) for a given analysis depends on the type of target species or analyte present in a sample. Various types of blocking buffers such as highly purified proteins, serum, or milk may be used to block free sites on a SAM. Additional blocking buffers include ethanolamine or polyethylene oxide (PEO)-containing materials. An ideal blocking buffer would bind to all potential sites of non-specific interaction away from an active region. To optimize a blocking buffer for a particular analysis, empirical testing may be used to determine signal-to-noise ratio. No single chemical or biological blocking material is ideal for every situation, since each antibody-antigen pair has unique characteristics.

FIGS. 3A-3D illustrate a fluidic device 60 (e.g., a biochemical sensor device) intended to serve as a comparison device to provide context for subsequently described embodiments of the disclosure. Such device 60 may be fabricated with laser-cut laminate layers to define a fluidic passage 52 bounded from below by a base structure including a BAW resonator structure, bounded laterally by a wall structure embodied in a pre-cut (e.g., laser cut) wall layer 44, and bounded from above by a cover or cap layer 46.

Figure 3A:
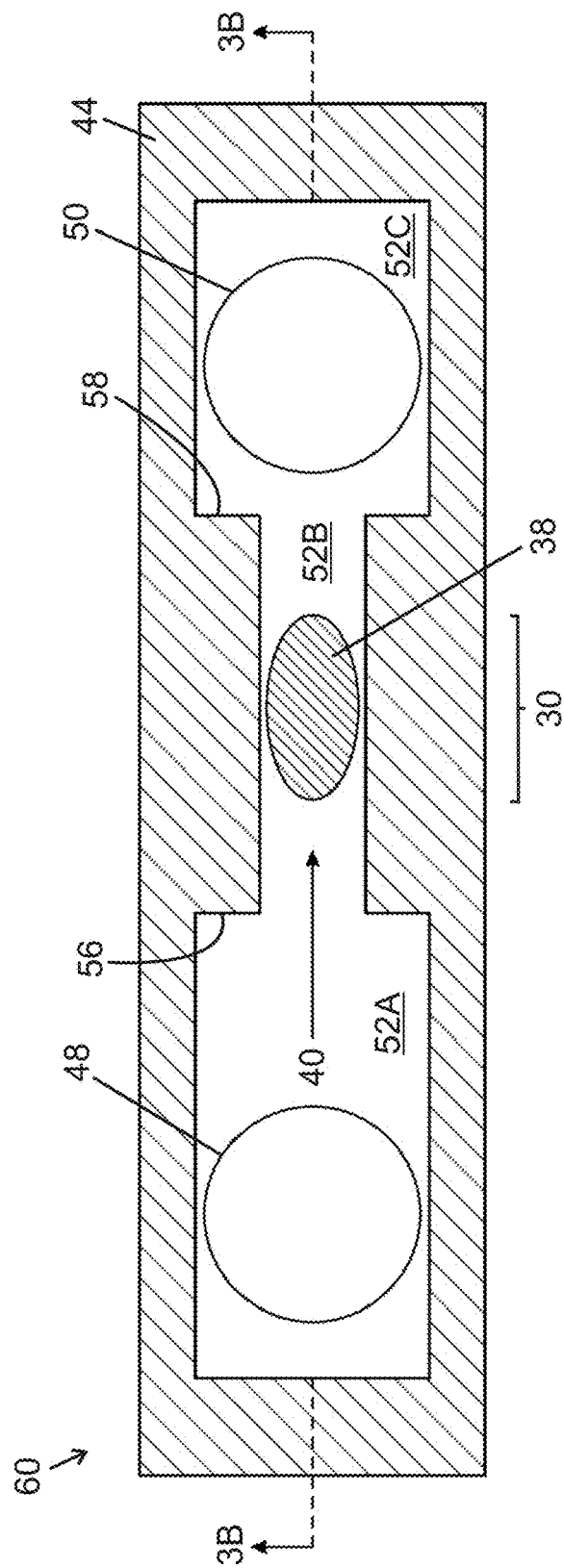
FIG. 3A is a schematic top plan view of a fluidic device including first and second fluidic ports arranged in fluid communication with a fluidic passage including a narrowed width intermediate segment containing an active region of a BAW MEMS resonator structure, with an arrow showing an intended direction of a flow of fluid through the fluidic device.

FIG. 3A is a schematic top plan view of the fluidic device 60 including first and second fluidic ports 48, 50 arranged in fluid communication with a fluidic passage 52 (labeled in FIG. 3B) composed of an upstream segment 52A, a narrowed width intermediate segment 52B, and a downstream segment 52C. Lateral boundaries of the segments 52A-52C are defined by a wall structure embodied in a wall layer 44. The intermediate segment 52B contains an active region 30 of a BAW MEMS resonator structure, and an arrow shows an intended direction of flow of a fluid volume 40 through the fluidic device 60. First and second shoulder regions 56, 58 are arranged upstream and downstream, respectively, of inwardly projecting sidewall portions and define transitions (i) between the upstream segment 52A and the intermediate segment 52B, and (ii) between the intermediate segment 52B and the downstream segment 52C, respectively. In certain embodiments, presence of the narrowed width intermediate segment 52B permits the active region 30 to extend across substantially an entire width of a portion (i.e., the intermediate segment 52B) of the fluidic passage 52, such that no portion of the fluid volume 40 flowing within the fluidic passage 52 may escape the fluidic device 60 without flowing over the active region 30 (thereby improving a likelihood of analyte binding). The size of the active region 30 is dictated at least in part by an intended operating frequency of the corresponding BAW resonator structure. Although the active region 30 is shown as having a predominantly oval shape oriented with a long dimension parallel to the intended direction of flow of the fluid volume 40, it is to be recognized that in certain embodiments, the active region 30 may be provided in any suitable shape and/or orientation, such as a round shape or an oval shape with a long dimension transverse to the intended direction of flow of the fluid volume 40.

Figure 3B:
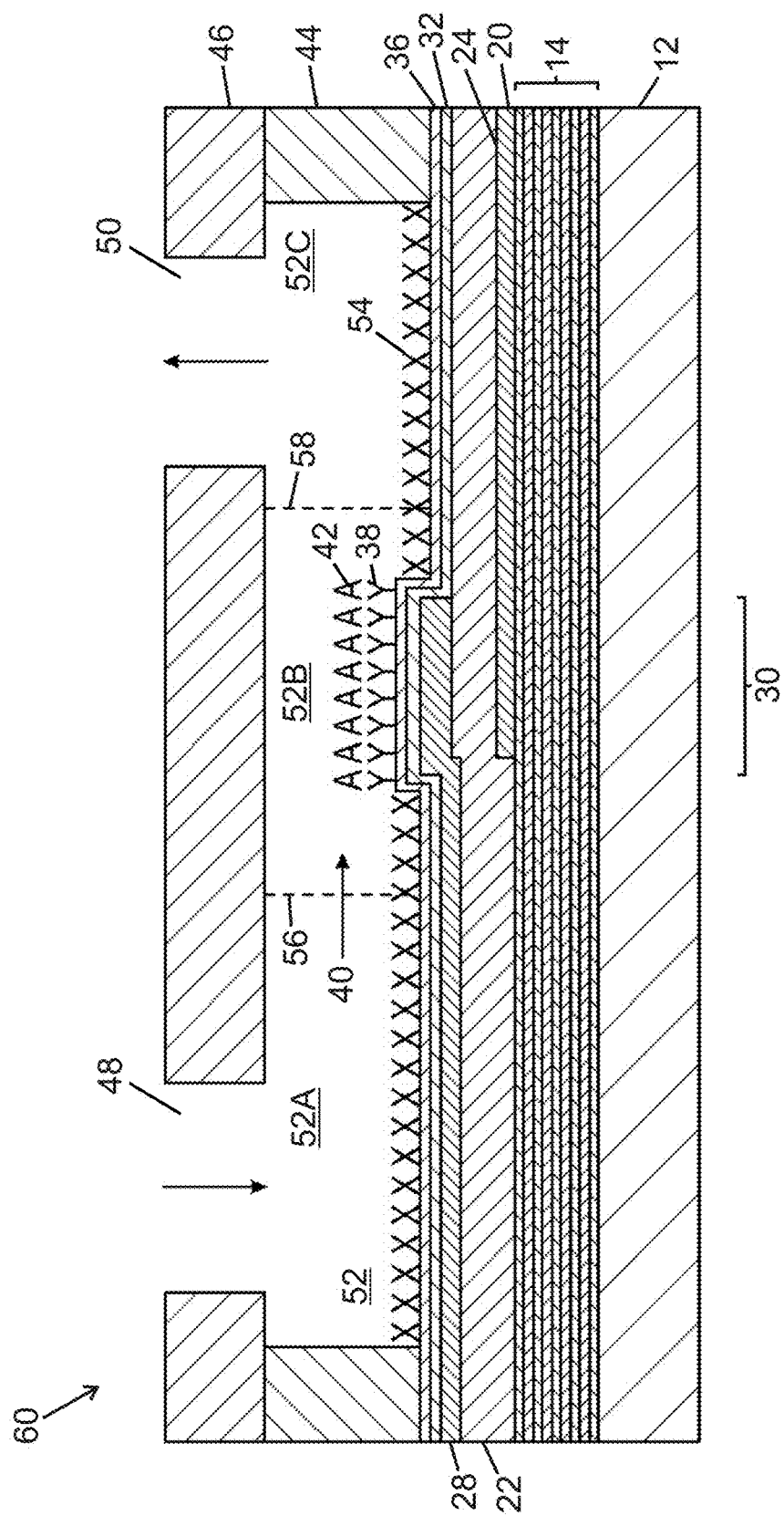
FIG. 3B is a schematic side cross-sectional view of the fluidic device of FIG. 3A taken along section line "3B-3B" shown in FIG. 3A.

FIG. 3B is a schematic side cross-sectional view of the fluidic device 60 of FIG. 3A taken along section line "3B-3B" shown in FIG. 3A. The fluidic device 60 includes a substrate 12 overlaid with an acoustic reflector 14, and a bottom side electrode 20 arranged generally below a piezoelectric material 22. A top side electrode 28 extends over a portion of the piezoelectric material 22, wherein a portion of the piezoelectric material 22 arranged between the top side electrode 28 and the bottom side electrode 20 embodies an active region 30 of the BAW resonator structure. The bottom side electrode 20 is arranged along a portion of a lower surface 24 of the piezoelectric material 22. The top side electrode 28 and the piezoelectric material 22 are overlaid with a hermeticity layer 32 and a self-assembled monolayer (SAM) 36. Portions of the SAM 36 between the active region 30 and the wall layer 44 are overlaid with a chemical or biological blocking material 54 to prevent localized attachment of functionalization material and/or analyte. A portion of the SAM 36 that is registered with the active region 30 is overlaid with a layer of functionalization (e.g., specific binding) material 38 arranged to bind at least one analyte 42. Walls of the wall layer 44 are laterally displaced from the active region 30 and extend upward from the SAM 36 to define lateral boundaries of the fluidic passage 52 containing the active region 30. More specifically, the active region 30 is provided in the intermediate segment 52B disposed between upstream and downstream segments 52A, 52C of the fluidic passage 52. The cover or cap layer 46 defines first and second fluidic ports 48, 50 (suitable for admitting fluid such as an analyte-containing sample) and further serves as an upper boundary for the fluidic passage 52. The cover or cap layer 46 may be formed by defining first and second fluidic ports 48, 50 (e.g., via laser cutting or water jet cutting) in a layer of an appropriate material (e.g., a substantially inert polymer, glass, silicon, ceramic, or the like), and adhering the cover or cap layer 46 to top surfaces of the wall layer 44.

During intended use of the fluidic device 60, a fluid volume 40 may be supplied through the first fluidic port 48 into upstream segment 52A of the fluidic passage 52, then flowed through the intermediate segment 52B over the active region 30, and then flowed through the downstream segment 52C to the second fluidic port 50 to exit the fluidic passage 52. Due to the laminar nature of the fluid flow within the fluidic passage 52, the fluid volume 40 may be modeled and behave as a "stack" of horizontal fluid layers. The analyte 42 contained in one or more lower layers of the fluid volume 40 may bind with functionalization material 38 arranged over the active region 30 in the intermediate segment 52B. Assuming that sufficient analyte 42 is present to bind with functionalization material 38 arranged over the active region 30, when a bulk acoustic wave having a dominant shear component is induced in the active region 30 by supplying an electrical (e.g., alternating current) signal of a desired frequency to the bottom and top side electrodes 20, 28, a change in electroacoustic response (e.g., at least one of an amplitude-magnitude property, a frequency property, or a phase property, such as a shift in resonant frequency) of the BAW resonator structure may be detected to indicate a presence and/or quantity of analyte 42 bound to the functionalization material 38.

In certain embodiments, the fluidic passage 52 may be microfluidic in scale, with at least one dimension (e.g., height and/or width) of no greater than about 500 microns, or about 250 microns, or about 100 microns. In such embodiments, the small dimensions of the fluidic passage 52 may render it susceptible to obstruction or blockage, such as by particulate material, cells, and/or bubbles that may be present in the fluid volume 40 supplied to the fluidic device 60. If dimensions of obstruction media exceed a smallest dimension of any segment of the fluidic passage 52, then the fluidic passage 52 may be fully blocked and rendered inoperable.

Figure 3C:
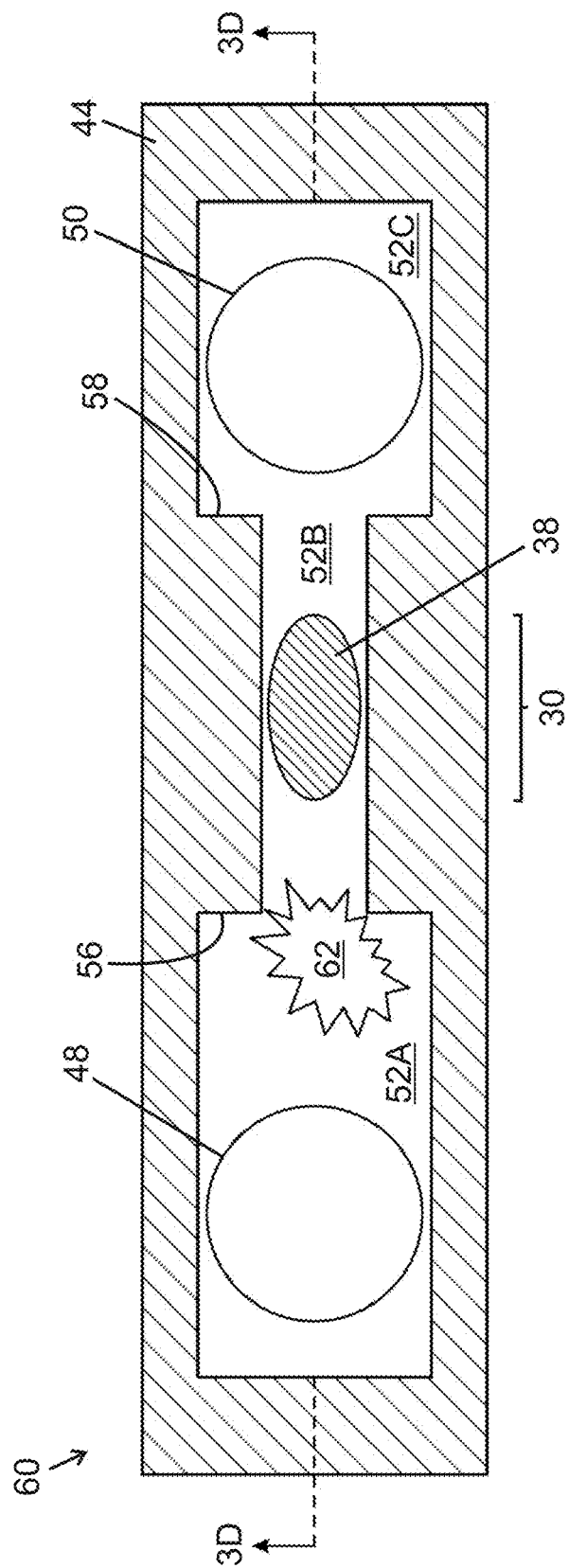
FIG. 3C is a schematic top plan view of the fluidic device of FIGS. 3A and 3B, showing an upstream end of the intermediate segment being blocked with obstruction media.
Figure 3D:
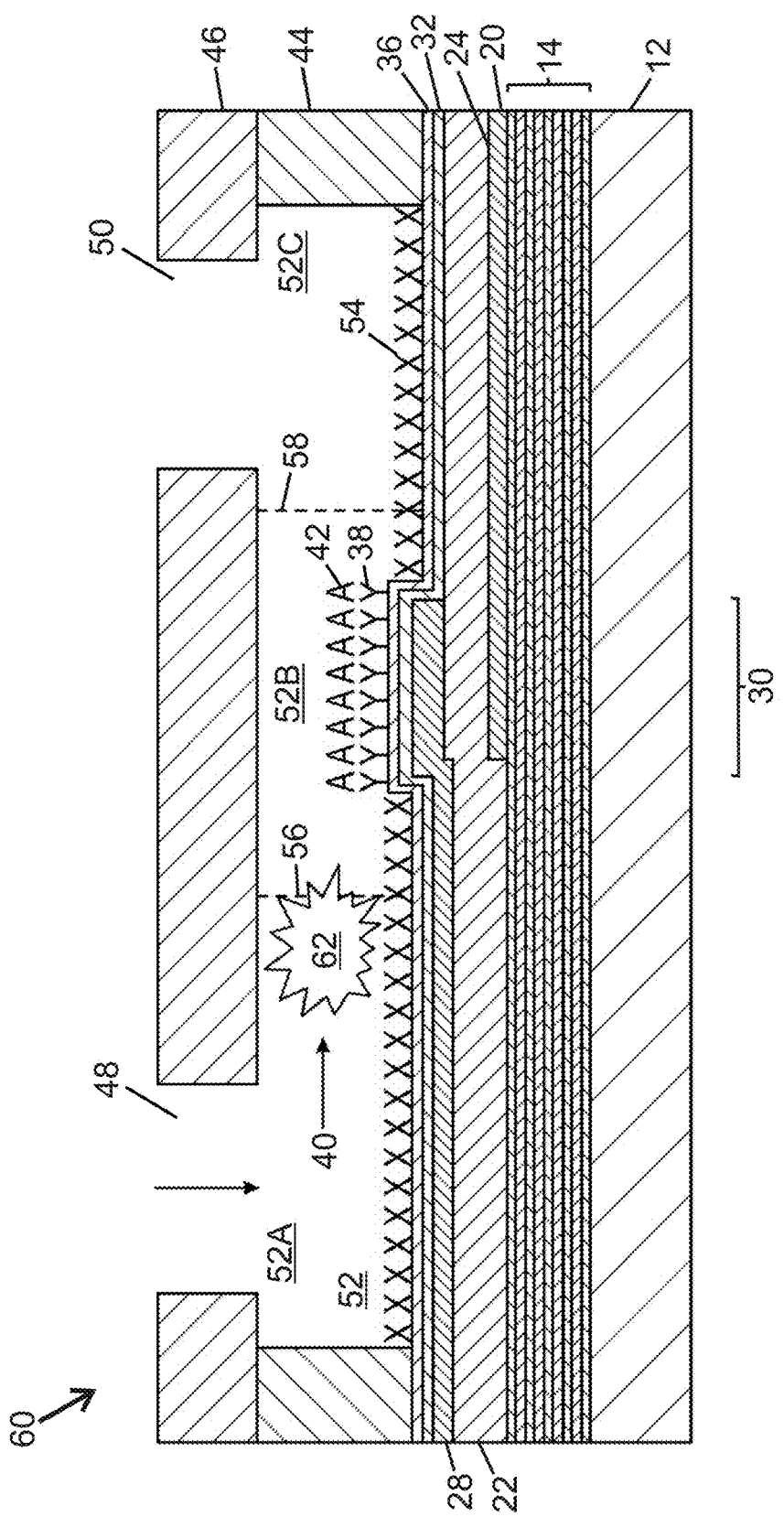
FIG. 3D is a schematic side cross-sectional view of the fluidic device of FIGS. 3A-3C taken along section line "3D-3D" shown in FIG. 3C, showing the upstream end of the intermediate segment being blocked with obstruction media.

FIGS. 3C and 3D provide schematic top plan and side cross-sectional views, respectively, of the fluidic device 60 disclosed in FIGS. 3A and 3B, with addition of obstruction media 62 at the first shoulder region 56 corresponding to a transition between the upstream segment 52A and the intermediate segment 52B. As shown, the obstruction media 62 serves to block passage of fluid through the fluidic passage 52. With the obstruction media 62 in this position, the fluidic device 60 is rendered inoperative, since analyte-containing fluid (e.g., fluid volume 40) is prevented from being supplied through the intermediate segment 52B to contact functionalization material 38 associated with the active region 30.

The above-described challenges associated with fluidic devices incorporating BAW resonator structures (e.g., biochemical sensor devices) have led to the development of fluidic devices incorporating BAW resonator structures with one or more features that provide filtration capability, as described hereinafter.

Figure 4A:
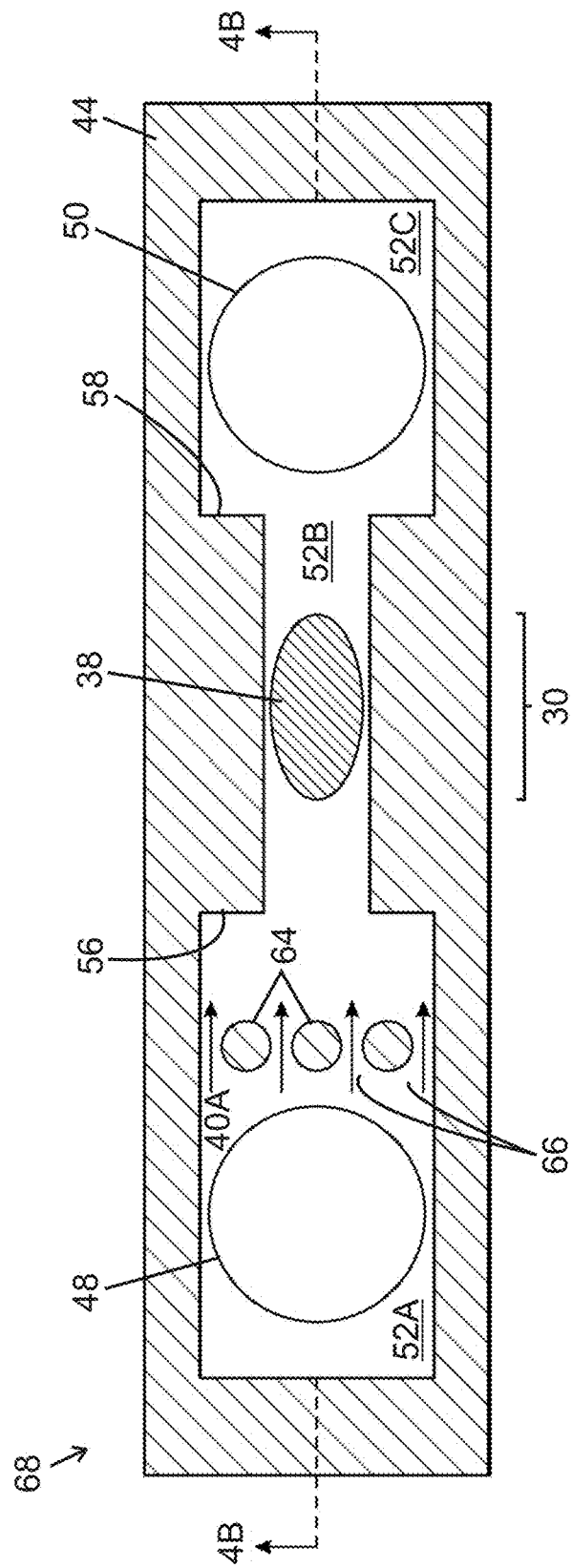
FIG. 4A is a schematic top plan view of a fluidic device including first and second fluidic ports arranged in fluid communication with a fluidic passage including a narrowed width intermediate segment containing an active region of a BAW MEMS resonator structure, with multiple vertically arranged pillars arranged between the first fluidic port and the intermediate segment and arrows showing parallel fluid flow paths between different pairs of pillars, according to one embodiment of the present disclosure.

FIG. 4A is a schematic top plan view of a fluidic device 68 including first and second fluidic ports 48, 50 arranged in fluid communication with a fluidic passage 52 (labelled in FIG. 4B) composed of a narrowed width intermediate segment 52B arranged between an upstream segment 52A and a downstream segment 52C. Lateral boundaries of the segments 52A-52C are defined by a wall structure embodied in a wall layer 44. The intermediate segment 52B contains an active region 30 of a BAW MEMS resonator structure, including functionalization material 38 arranged over the active region 30. First and second shoulder regions 56, 58 are arranged upstream and downstream, respectively, of inwardly projecting sidewall portions and define transitions (i) between the upstream segment 52A and the intermediate segment 52B, and (ii) between the intermediate segment 52B and the downstream segment 52C, respectively. Within the upstream segment 52A, between the first fluidic port 48 and the first shoulder region 56, multiple pillars 64 extend in a vertical direction into the upstream segment 52A, and are arranged in a line extending transverse to a longitudinal axis of the fluidic device 68 that extends through the first and second fluidic ports 48, 50. The pillars 64 are spaced apart from one another by inter-pillar spaces 66 that enable passage of parallel fluid streams 40A (shown by arrows) of fluid between different pairs of pillars 64, with such fluid being supplied to the fluidic device 68 through the first fluidic port 48. As shown in FIG. 4A, the pillars 64 are equally sized and equally spaced relative to one another.

Figure 4B:
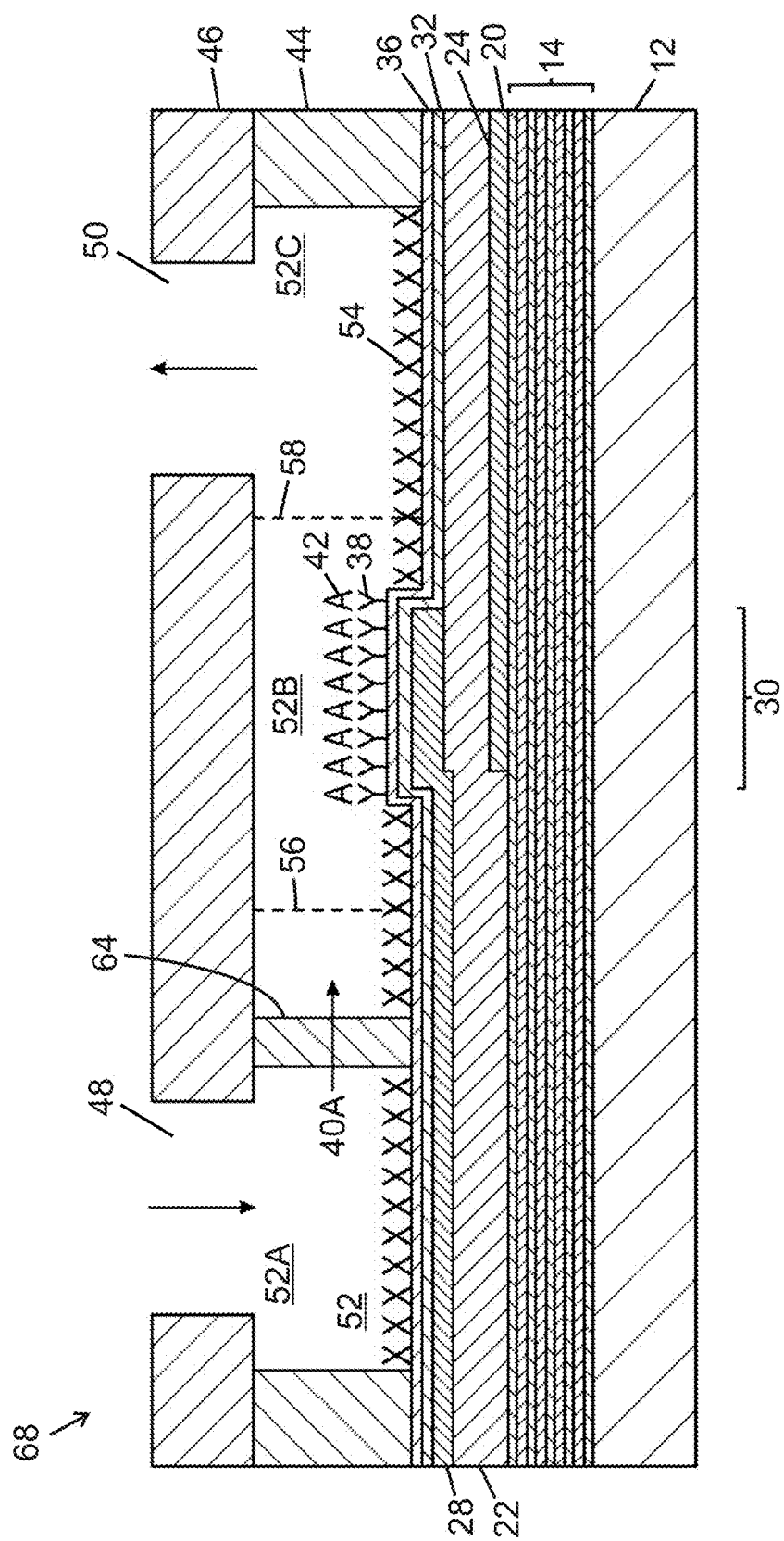
FIG. 4B is a schematic side cross-sectional view of the fluidic device of FIG. 4A taken along section line "4B-4B" shown in FIG. 4A.

FIG. 4B is a schematic side cross-sectional view of the fluidic device 68 of FIG. 4A taken along section line "4B-4B" shown in FIG. 4A. Each feature shown in FIG. 4B is identical to the corresponding features shown in FIG. 3B, except for the addition of pillars 64 and presence of an arrow corresponding to parallel fluid streams 40A. For the sake of brevity, the detailed description of features of FIG. 3B hereinabove is hereby incorporated by reference with respect to FIG. 4B.

In operation of the fluidic device 68 of FIGS. 4A and 4B, a fluid volume may be supplied through a first fluidic port 48 into the upstream segment 52A of the fluidic passage 52. Upon reaching the pillars 64, the fluid volume is divided into multiple parallel streams 40A (e.g., four parallel fluid streams as illustrated in FIG. 4A) as it flows through inter-pillar spaces 66 (shown in FIG. 4A). Thereafter, the parallel fluid streams 40A recombine into the single fluid volume that flows through the intermediate segment 52B over the active region 30, and then flows through the downstream segment 52C to the second fluidic port 50 to exit the fluidic passage 52. An analyte 42 contained in one or more lower layers of the fluid volume may bind with functionalization material 38 arranged over the active region 30 in the intermediate segment 52B. Assuming that sufficient analyte is present to bind with functionalization material 38 arranged over the active region 30, when a bulk acoustic wave having a dominant shear component is induced in the active region 30 by supplying an electrical (e.g., alternating current) signal of a desired frequency to the bottom and top side electrodes 20, 28, a change in electroacoustic response (e.g., at least one of an amplitude-magnitude property, a frequency property, or a phase property, such as a shift in resonant frequency) of the BAW resonator structure may be detected to indicate a presence and/or quantity of analyte 42 bound to the functionalization material 38.

Presence of multiple pillars 64 in the upstream segment 52A of the fluidic passage 52 of the fluidic device 68 provides multiple redundant flow paths, corresponding to the inter-pillar spaces 66, to permit passage of parallel fluid streams 40A. If one flow path (corresponding to one inter-pillar space 66') is blocked by presence of obstruction media, then other flow paths provided by other inter-pillar spaces 66 may remain open to prevent complete blockage of the fluidic passage 52. Such a phenomenon is shown in FIGS. 4C and 4D.

Figure 4C:
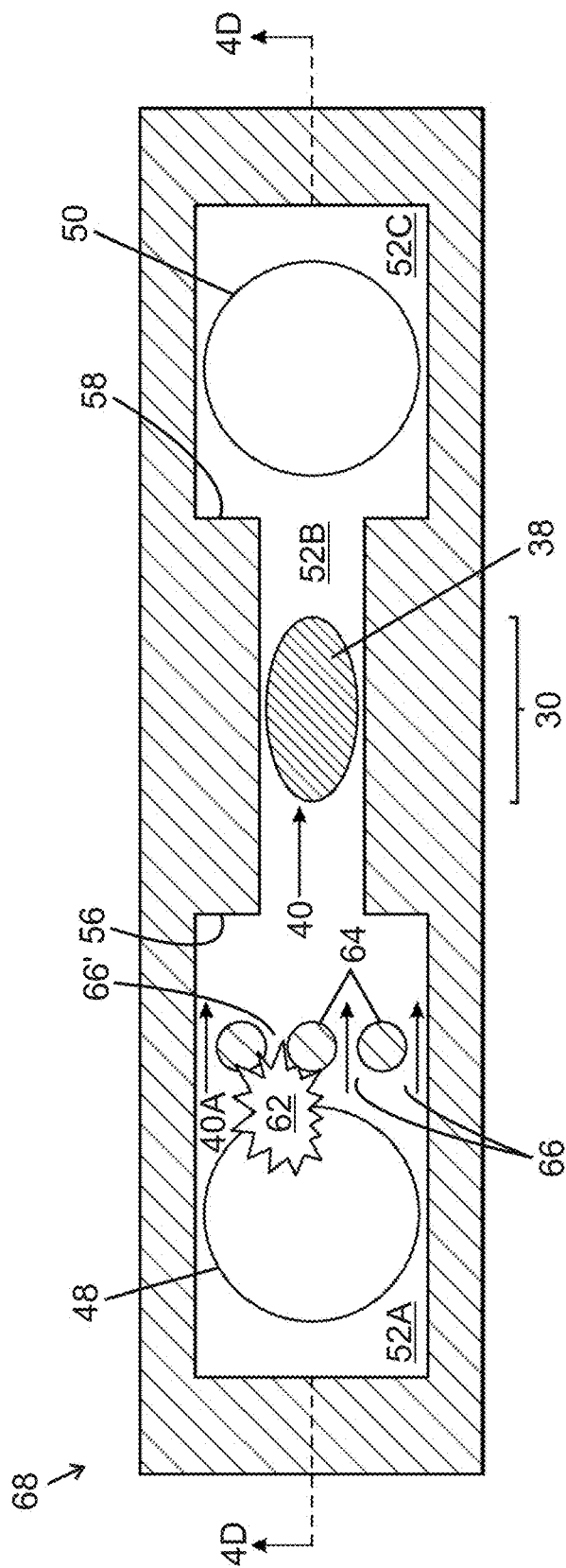
FIG. 4C is a schematic top plan view of the fluidic device of FIGS. 4A and 4B, showing obstruction media occluding one fluid flow path of the parallel fluid flow paths, with other parallel fluid flow paths remaining unobstructed.
Figure 4D:
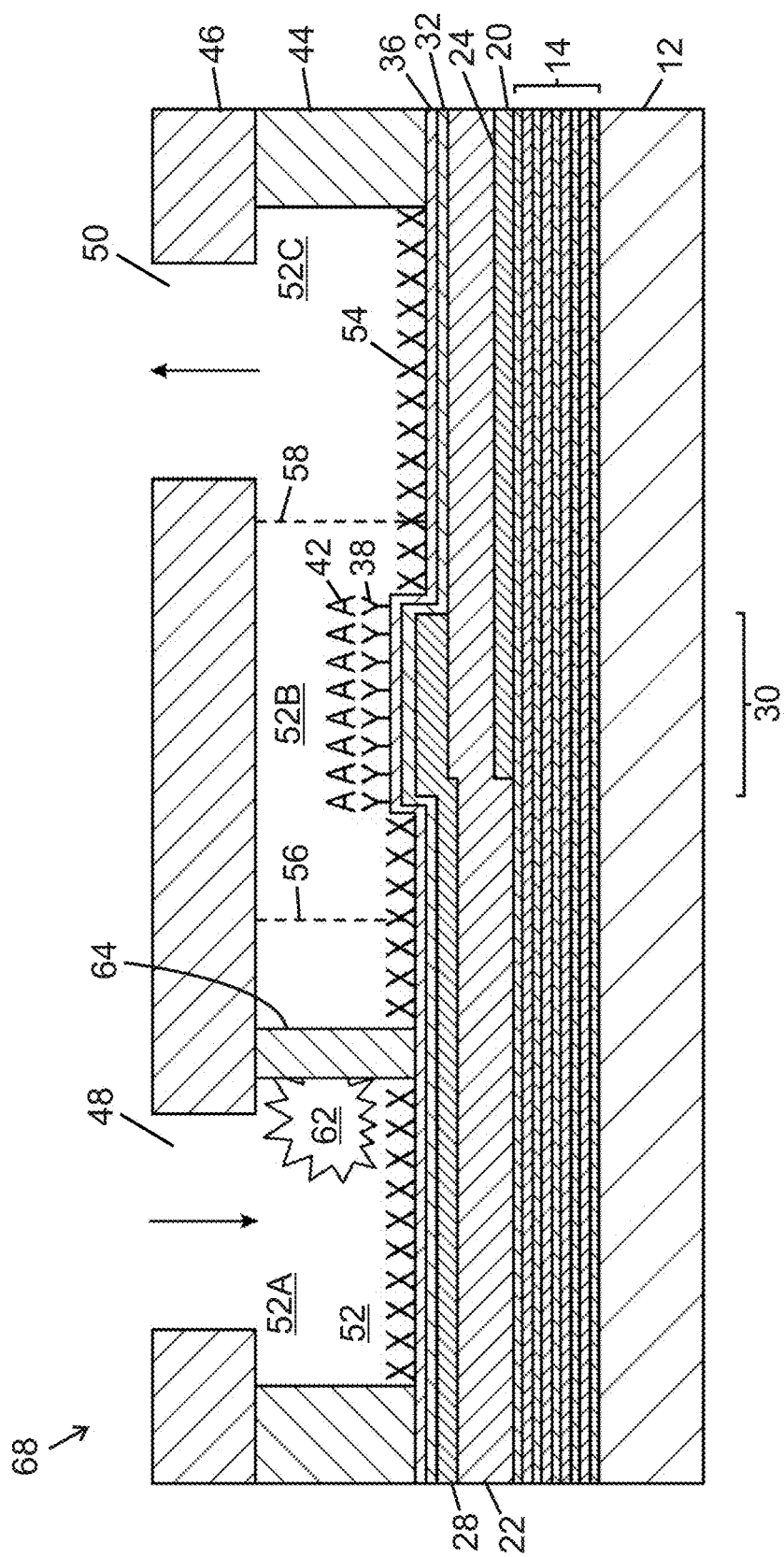
FIG. 4D is a schematic side cross-sectional view of the fluidic device of FIGS. 4A-4C taken along section line "4D-4D" shown in FIG. 4C, showing obstruction media occluding one fluid flow path of the parallel fluid flow paths.

FIGS. 4C and 4D provide schematic top plan and side cross-sectional views, respectively, of the fluidic device 68 disclosed in FIGS. 4A and 4B, with addition of obstruction media 62 in one inter-pillar space 66' between two pillars 64 of the multiple pillars 64 that extend in a transverse line across the upstream segment 52A between the first fluidic port 48 and the first shoulder region 56 (serving as a transition to the intermediate segment 52B). Although the obstruction media 62 may block passage of fluid through one inter-pillar space 66', the presence of other flow paths provided by other inter-pillar spaces 66 permits passage of parallel fluid streams 40A past the pillars 64 and into the intermediate segment 52B to flow over the active region 30. Unless all of the inter-pillar spaces 66 are blocked by obstruction media 62, fluid flow should remain viable through the fluidic passage 52 of the fluidic device 68 due to the existence of redundant flow paths.

In certain embodiments, each pillar may extend 100% of a height of a fluidic passage (or segment thereof) between a base structure and a cover structure of a fluidic device. In certain embodiments, each pillar may extend a height that is at least about 50%, at least about 60%, at least about 70%, at least about 80%, or at least about 90% of a height (or an average height) of a fluidic passage or a segment thereof. In certain embodiments, a plurality of pillars extends upward from the base structure. In certain embodiments, a plurality of pillars extends downward from the cover structure.

Although pillars of cylindrical shapes are illustrated in various figures herein, it is to be recognized that pillars may comprise any suitable shape. In certain embodiments, pillars may include cross-sectional shapes that are circular, oval-shaped, rectangular, trapezoidal, or teardrop-shaped when viewed from above. In certain embodiments, pillars may include cross-sectional dimensions that are uniform over the entire height(s) thereof. In other embodiments, one or more pillars may include cross-sectional dimensions that vary with respect to pillar height. For example, one or more pillars may be frustoconical in shape with a width that tapers with position over the height of the pillar(s).

In certain embodiments, a plurality of pillars may be arranged in one or more linear rows within a fluidic passage. In certain embodiments, one or more linear rows of pillars may be arranged transverse to, or arranged at an angle between 10 degrees and 80 degrees relative to, a longitudinal axis of bulk flow of fluid through a fluidic device. In certain embodiments, a plurality of pillars may be arranged in a chevron shape or an arc shape within a fluidic passage, with an apex of the chevron shape or arc shape arranged closer to an upstream fluidic port than to a downstream fluidic port. In other embodiments, an apex of the chevron shape or arc shape may be arranged closer to an downstream fluidic port than to a upstream fluidic port.

In certain embodiments, multiple groups of pillars may be sequentially arranged within a fluidic passage. In certain embodiments, a first group of pillars may include a first inter-pillar spacing, and a second group of pillars downstream of the first group of pillars may include a second inter-pillar spacing, wherein the first inter-pillar spacing is greater than the second inter-pillar spacing. Such an arrangement may permit large obstruction media to be restrained by the first group of pillars, and permit smaller obstruction media to be restrained by the second group of pillars, without the smaller obstruction media being aggregated behind the larger obstruction media. Such an arrangement may delay or prevent blockage of fluid flow through a fluidic device.

In certain embodiments, one or more groups of pillars may include uniform inter-pillar spacing. In certain embodiments, one or more groups of pillars may include non-uniform inter-pillar spacing.

Various methods may be used to form one or more groups of pillars, such as by subtractive material removal processes (e.g., etching, laser micromachining, etc.), and/or an additive manufacturing process (e.g., involving deposition of materials such as SU-8, photoresist, Parylene, epoxy, polymers, etc., by three-dimensional printing, laser micromachining, selective deposition, and the like). In certain embodiments, one or more material removal or deposition steps may employ, or may be preceded by, photolithographic patterning. In certain embodiments, one or more groups of pillars may be produced by selective impingement of radiation on a photocurable material. In certain embodiments, one or more groups of pillars may comprise at least one of a photosensitive material, photoresist, or epoxy.

In certain embodiments, pillars may be formed prior to, or after, application of one or more of the following items over a base structure: a hermeticity layer, an interface layer, a self-assembled monolayer, a blocking material, or any other desired layer.

Figure 5A:
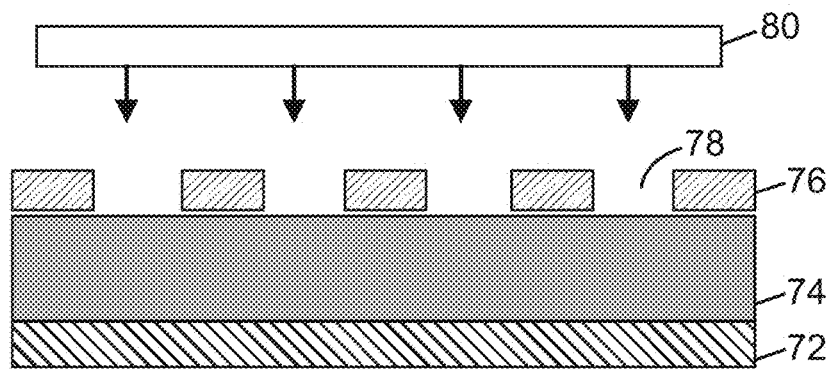
FIGS. 5A-5D provide schematic cross-sectional views of raised pillars producible by selective impingement of radiation on a photocurable material in various states of formation, according to one embodiment.
Figure 5B:
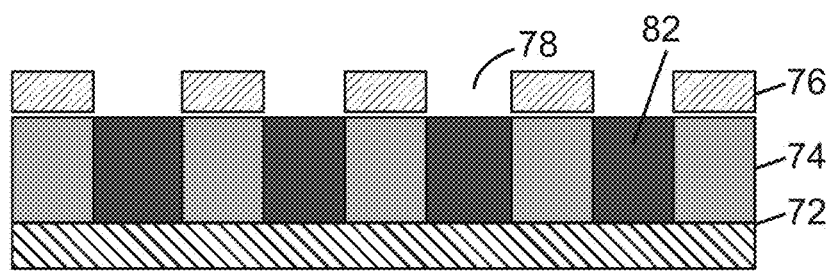
Figure 5C:
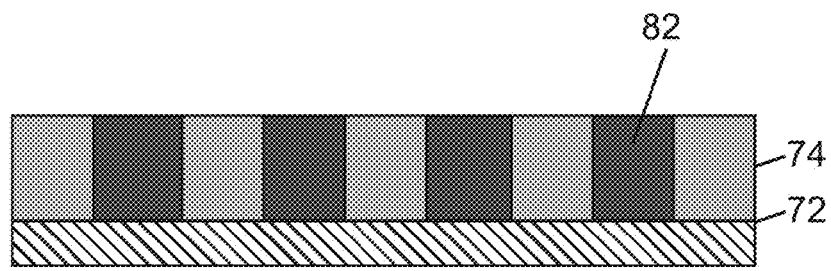
Figure 5D:
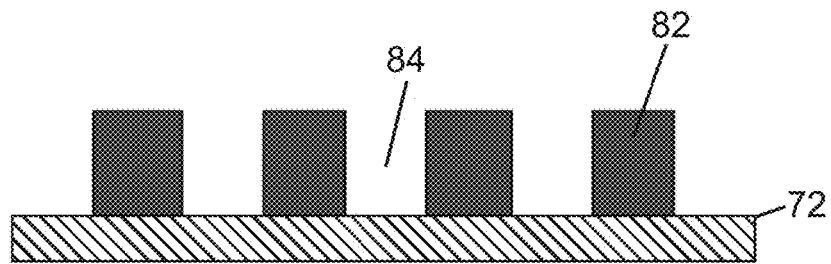

FIGS. 5A-5D provide schematic cross-sectional views of raised pillars producible by selective impingement of radiation on a photocurable material in various states of formation, according to one embodiment. FIG. 5A illustrates an interface layer 72 (which may optionally embody any layer associated with a base structure of a fluidic device, or embody a cover structure) overlaid with a layer of photocurable material 74, with a photomask 76 defining mask windows 78 arranged between the photocurable material 74 and an electromagnetic (e.g., ultraviolet) radiation source 80. FIG. 5B illustrates the photomask 76, interface layer 72, and layer of photocurable material 74 following impingement of radiation through the mask windows 78 to form cured regions 82 in the layer of photocurable material 74. FIG. 5C illustrates the interface layer 72 and selectively cured layer of photocurable material 74 following removal of the photomask 76. FIG. 5D shows the structure of FIG. 5C following removal of uncured portions of the photocurable material 74 (e.g., by dissolution and rinsing), yielding multiple vertically extending cured regions 82 separated by gaps 84. The vertically extending cured regions 82 may serve as pillars within a fluidic device as disclosed herein.

Figure 6A:
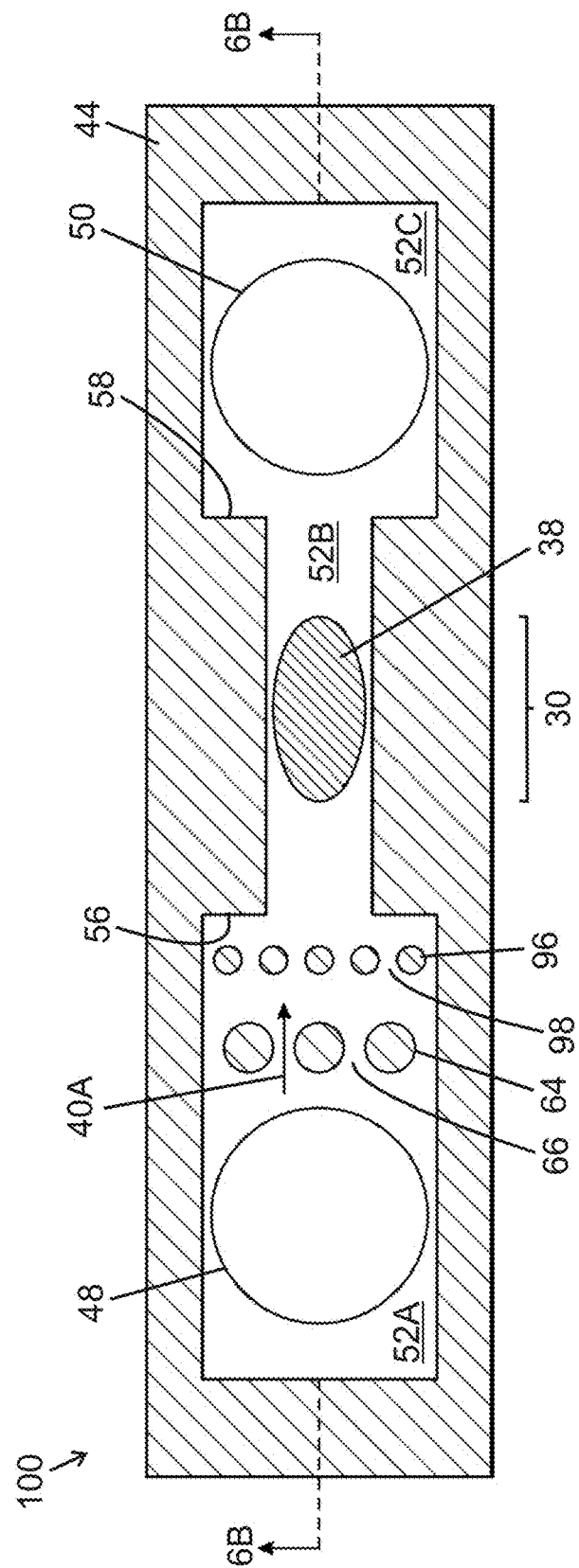
FIG. 6A is a schematic top plan view of a fluidic device including first and second fluidic ports arranged in fluid communication with a fluidic passage including a narrowed width intermediate segment containing an active region of a BAW MEMS resonator structure, with two rows of differently-sized vertically arranged pillars arranged between the first fluidic port and the intermediate segment, according to one embodiment of the present disclosure.
Figure 6B:
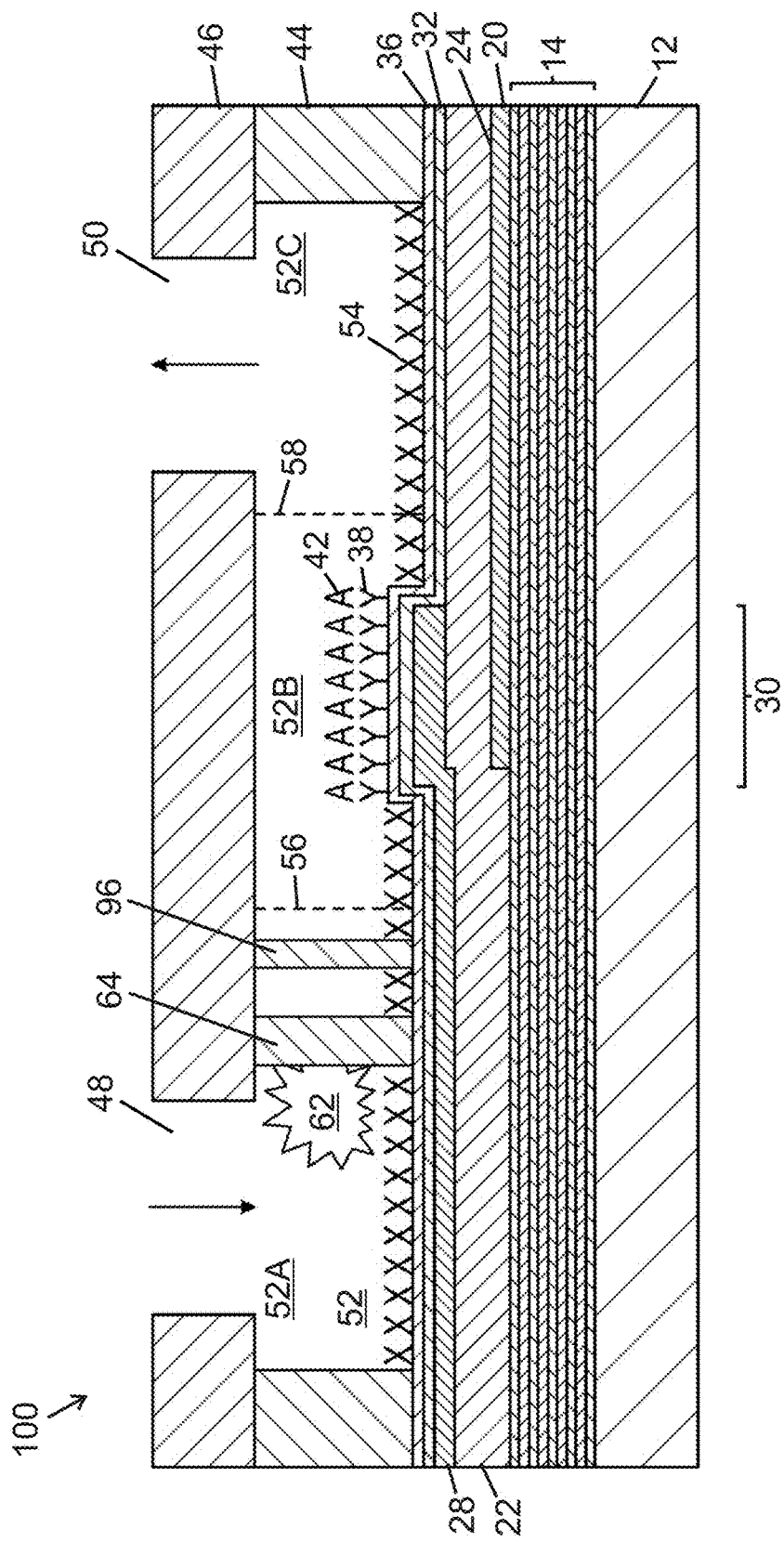
FIG. 6B is a schematic side cross-sectional view of the fluidic device of FIG. 6A, taken along section line "6B-6B" shown in FIG. 6A, showing obstruction media occluding one fluid flow path between two pillars of a first row of pillars.

In certain embodiments, multiple rows of differently-sized vertically extending pillars may be provided in a single fluidic device. FIGS. 6A and 6B provide schematic top plan and side cross-sectional views, respectively, of a fluidic device 100 including two rows of differently-sized vertically arranged pillars 64, 96 arranged within an upstream segment 52A of a fluidic passage 52. The fluidic device 100 includes first and second fluidic ports 48, 50 arranged in fluid communication with the fluidic passage 52, which is composed of a narrowed width intermediate segment 52B arranged between the upstream segment 52A and a downstream segment 52C. Lateral boundaries of the segments 52A-52C are defined by a wall structure embodied in a wall layer 44. The intermediate segment 52B contains an active region 30 of a BAW MEMS resonator structure, including functionalization material 38 arranged over the active region 30. First and second shoulder regions 56, 58 are arranged upstream and downstream, respectively, of inwardly projecting sidewall portions and define transitions (i) between the upstream segment 52A and the intermediate segment 52B, and (ii) between the intermediate segment 52B and the downstream segment 52C, respectively. The two rows of vertically arranged pillars 64, 96 are positioned within the upstream segment 52A, between the first fluidic port 48 and the first shoulder region 56, with each row of pillars 64, 96 arranged in a line extending transverse to a longitudinal axis of the fluidic device 100 that extends through the first and second fluidic ports 48, 50. Pillars 64 within the first row are separated by inter-pillar spaces 66, and pillars 96 within the second row are separated by inter-pillar spaces 98, with the respective inter-pillar spaces 66, 98 enabling passage of parallel fluid streams 40A (shown in FIG. 6A) of fluid supplied to the fluidic device 100 through the first fluidic port 48. As shown in FIG. 6A, pillars 64 within the first row are larger and fewer in number than pillars 96 within the second row, and inter-pillar spaces 66 defined between pillars 64 of the first row are larger than the inter-pillar spaces 98 defined between pillars 96 of the second row. FIG. 6B shows obstruction media 62 retained between pillars 64 of the first row, occluding one inter-pillar space between two pillars 64, but permitting fluid to flow between other inter-pillar spaces of the first and second rows of pillars 64, 96. Aside from the inclusion of an additional row of pillars 96, the fluidic device 100 of FIGS. 6A and 6B is substantially similar to the fluidic device 68 disclosed in connection with FIGS. 4A and 4B, such that the descriptions hereinabove of FIGS. 4A and 4B are incorporated by reference rather than repeated. Operation of the fluidic device 100 of FIGS. 6A and 6B is also substantially similar to operation of the fluidic device 68 of FIGS. 4A and 4B as described hereinabove.

Figure 7:
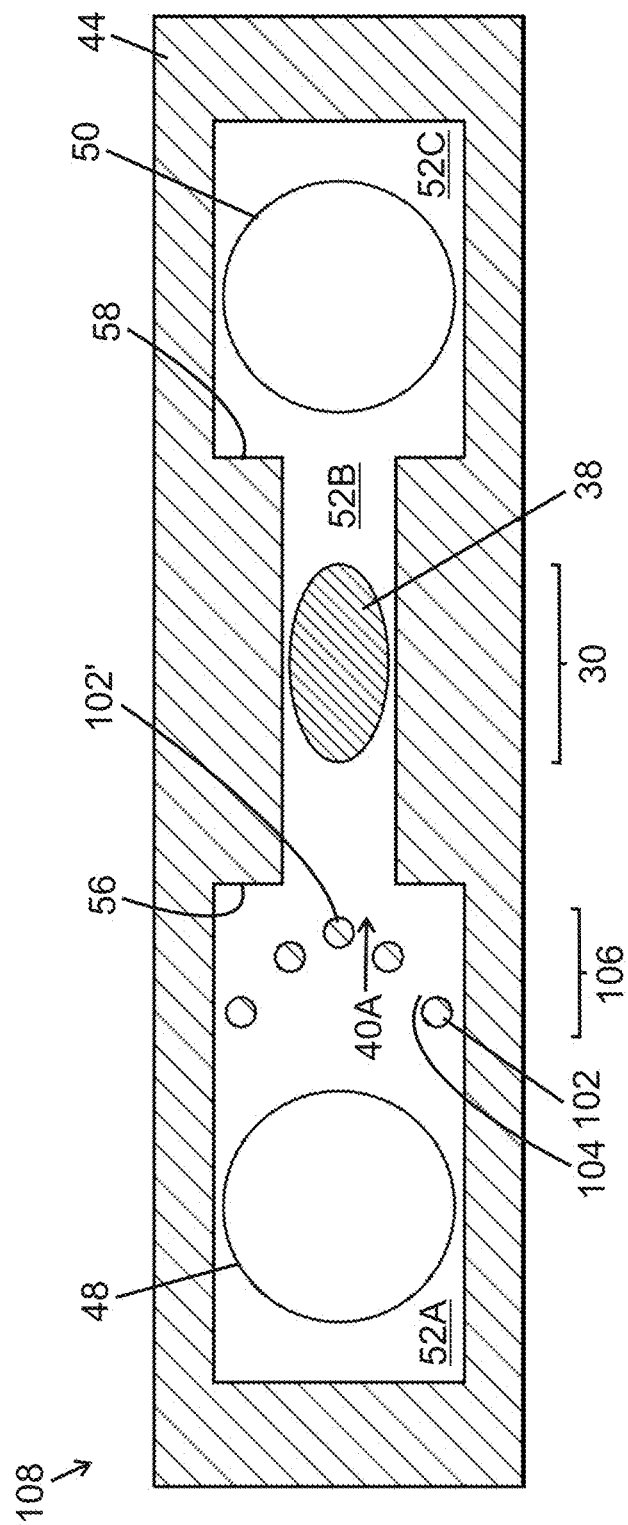
FIG. 7 is a schematic top plan view of a fluidic device including first and second fluidic ports arranged in fluid communication with a fluidic passage including a narrowed width intermediate segment containing an active region of a BAW MEMS resonator structure, and a crescent-shaped arrangement of vertically extending pillars positioned between the first fluidic port and the intermediate segment, according to one embodiment of the present disclosure.

FIG. 7 is a schematic top plan view of a fluidic device 108 including first and second fluidic ports 48, 50 arranged in fluid communication with a fluidic passage composed of upstream segment 52A, a narrowed width intermediate segment 52B, and a downstream segment 52C, with a crescent-shaped arrangement 106 of vertically extending pillars 102 positioned in the upstream segment 52A downstream of the first fluidic port 48. Lateral boundaries of the segments 52A-52C are defined by a wall structure embodied in a wall layer 44. The pillars 102 are separated by inter-pillar spaces 104 that enable passage of parallel fluid streams 40A of fluid supplied to the fluidic device 108 through the first fluidic port 48. First and second shoulder regions 56, 58 are arranged upstream and downstream, respectively, of inwardly projecting sidewall portions and define transitions (i) between the upstream segment 52A and the intermediate segment 52B, and (ii) between the intermediate segment 52B and the downstream segment 52C, respectively. An active region 30 of a BAW resonator structure including functionalization material 38 arranged thereover is positioned within the intermediate segment 52B. Arrangement of the pillars 102 in a crescent formation 106 enables obstruction media (not shown) to be directed to a center of the upstream segment 52A (e.g., against a centermost pillar 102') when fluid is flowing through the fluidic passage. Operation of the fluidic device 108 of FIG. 7 is substantially similar to operation of the fluidic device 68 of FIGS. 4A and 4B as described hereinabove.

Figure 8:
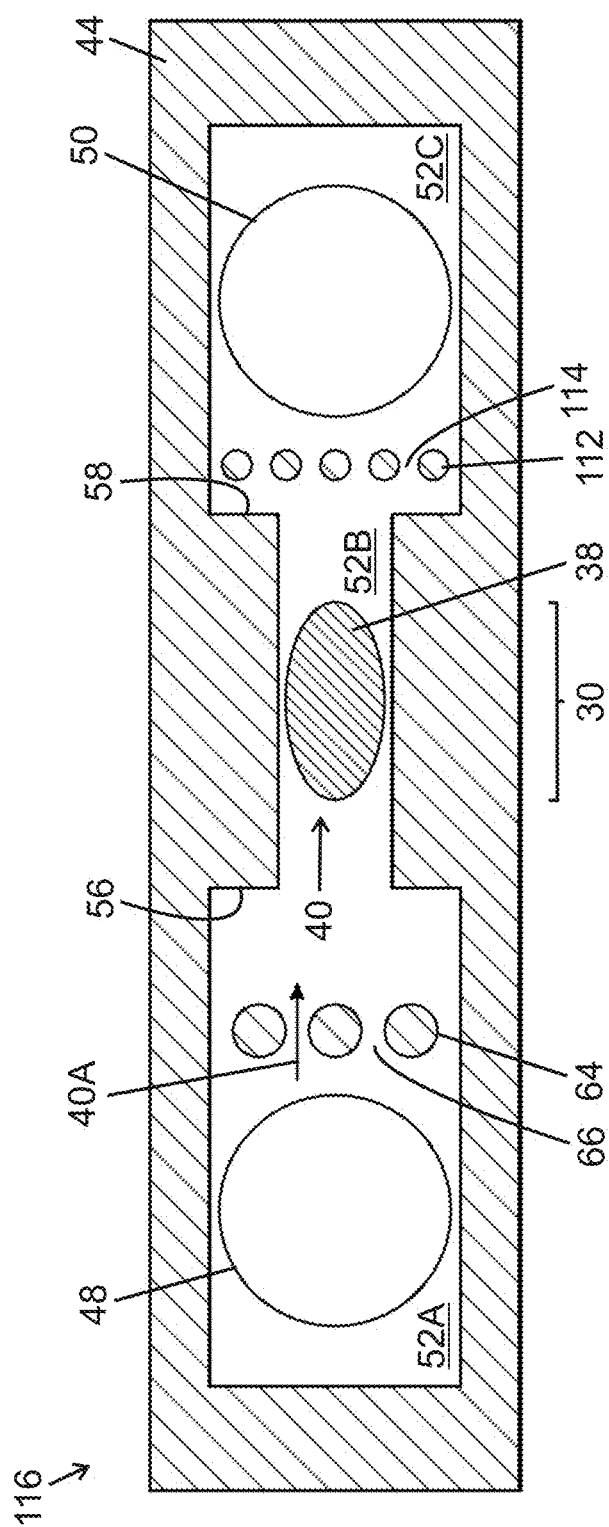
FIG. 8 is a schematic top plan view of a fluidic device including first and second fluidic ports arranged in fluid communication with a fluidic passage including a narrowed width intermediate segment containing an active region of a BAW MEMS resonator structure, an upstream group of vertically extending pillars arranged upstream of the active region, and a downstream group of vertically extending pillars arranged downstream of the active region, according to one embodiment of the present disclosure.

In certain embodiments, a first group of pillars may be arranged upstream of an active region and a second group of pillars may be arranged downstream of an active region of a fluidic device as described herein. For example, FIG. 8 illustrates a fluidic device 116 including first and second fluidic ports 48, 50 arranged in fluid communication with a fluidic passage composed of upstream segment 52A, a narrowed width intermediate segment 52B, and a downstream segment 52C, with a first group of vertically extending pillars 64 positioned in the upstream segment 52A (i.e., downstream of the first fluidic port 48), and with a second group of vertically extending pillars 112 positioned in the downstream segment 52C (i.e., upstream of the second fluidic port 50). Pillars 64 within the first group are separated by inter-pillar spaces 66, and pillars 112 within the second group are separated by inter-pillar spaces 114, with the respective inter-pillar spaces 66, 114 enabling passage of parallel fluid streams 40A of fluid supplied to the fluidic device 116 through the first fluidic port 48. First and second shoulder regions 56, 58 are arranged upstream and downstream, respectively, of inwardly projecting sidewall portions and define transitions (i) between the upstream segment 52A and the intermediate segment 52B, and (ii) between the intermediate segment 52B and the downstream segment 52C, respectively. An active region 30 of a BAW resonator structure including functionalization material 38 arranged thereover is positioned within the intermediate segment 52B. Lateral boundaries of the segments 52A-52C are defined by a wall structure embodied in a wall layer 44. Each row of pillars 64, 112 is arranged in a line extending transverse to a longitudinal axis of the fluidic device 116 that extends through the first and second fluidic ports 48, 50. As shown, pillars 64 within the first group are larger and fewer in number than pillars 112 within the second group, and inter-pillar spaces 66 defined between pillars 64 of the first group are larger than the inter-pillar spaces 114 defined between pillars 112 of the second group.

In operation of the fluidic device 116 of FIG. 8, a fluid volume 40 may be supplied through the first fluidic port 48 into the upstream segment 52A. Upon reaching the pillars 64, the fluid volume 40 is divided into multiple parallel streams 40A (e.g., four parallel streams) as it flows through the inter-pillar spaces 66. Thereafter, the parallel streams 40A recombine into a single fluid volume 40 that flows through the intermediate segment 52B over the active region 30, and then flows through inter-pillar spaces 114 of the second group of pillars 112 to reach the second fluidic port 50 and exit fluidic device 116. An analyte contained in the fluid volume 40 may bind with functionalization material 38 arranged over the active region 30 in the intermediate segment 52B. Assuming that sufficient analyte is present to bind with functionalization material 38 arranged over the active region 30, when a bulk acoustic wave having a dominant shear component is induced in the active region 30 by supplying an electrical (e.g., alternating current) signal of a desired frequency to electrodes of the BAW resonator structure, a change in electroacoustic response (e.g., at least one of an amplitude-magnitude property, a frequency property, or a phase property, such as a shift in resonant frequency) of the BAW resonator structure may be detected to indicate a presence and/or quantity of analyte bound to the functionalization material 38.

In certain embodiments, the inter-pillar spaces 114 defined by the second group of pillars 112 may be smaller than the size of an analyte (e.g., target species) within fluid supplied to the fluidic device 116 in a direction from the first fluidic port 48 to the second fluidic port 50 to intentionally trap any analyte (i.e., analyte not bound to functionalization material 38 overlying the active region 30 following initial flow of fluid through the intermediate segment 52B) between the active region 30 and the second group of pillars 112. After a specified time, a specified cumulative flow, an accumulation of target species, and/or attainment of a specified backpressure condition, fluid flow may be reversed (i.e., in a direction from the second fluidic port 50 to the first fluidic port 48) to cause accumulated analyte to flow (again) over the active region 30 and permit binding during a second (or subsequent) pass of analyte over the functionalization material 38. In this manner, the second group of pillars 112 may function as an analyte concentrator, which may be advantageous in situations with low analyte concentration and/or slow rate of binding to functionalization material 38 overlying the active region 30.

In other embodiments, first and second groups of pillars 64, 112 as shown in FIG. 8 may permit the fluidic device 116 to filter fluid in either direction (i.e., providing bidirectional flow capability) without necessarily providing analyte concentration utility.

Although various embodiments disclosed herein are directed to fluidic devices incorporating BAW resonator structures (e.g., biosensors) with vertically extending pillars that provide filtration capability, in other embodiments, filtration capability may be provided with one or more porous materials. In certain embodiments, a porous material may include a mesh, a porous membrane, a fibrous material, a perforated material, a woven fabric, a non-woven material, or the like. In certain embodiments, one or more porous materials may include permeable polymeric membranes (e.g., including polyolefins (such as polyethylene or polypropylene), polytetrafluoroethylene, PEEK, or the like), track-etched membranes, and stretched polymer films. Various permeable polymeric membranes are commercially available from Pall Corporation (Port Washington, N.Y., US), American Profol Inc. (Cedar Rapids, Iowa, US), Porex Technologies Corp. (Fairburn, Ga., US), and Novamem AG (Schlieren, Switzerland). In certain embodiments, porous materials such as membranes may be surface modified (e.g., with chemical, plasma, or other conventional means) to enhance bonding with adjacent layers when utilized in a multi-layer microfluidic device or cartridge. Porous materials may be selected for desired applications based on criteria such as pore size, thickness, compatibility with carrier fluids and/or analytes, and hydrophobicity or hydrophilicity. In certain embodiments, porous materials may be functionalized to promote selective removal of one or more constituents of a sample volume prior to passage over an active region of a BAW resonator structure of a fluidic device disclosed herein.

In certain embodiments, one or more porous materials may be arranged in or on a cover structure of a fluidic device that includes a BAW resonator structure. In certain embodiments, one or more porous materials may be arranged upstream of such a cover structure. In certain embodiments, the porous material is arranged in a filtration cartridge that is distinct and separable from the cover structure. In certain embodiments, a porous material may be arranged (e.g., mechanically compressed, adhered, or thermally bonded) between first and second non-porous structures (e.g., layers) defining openings therein, with the openings being registered with one another to permit fluid to flow through one opening, then through the porous material, and then through the other opening.

Figure 9:
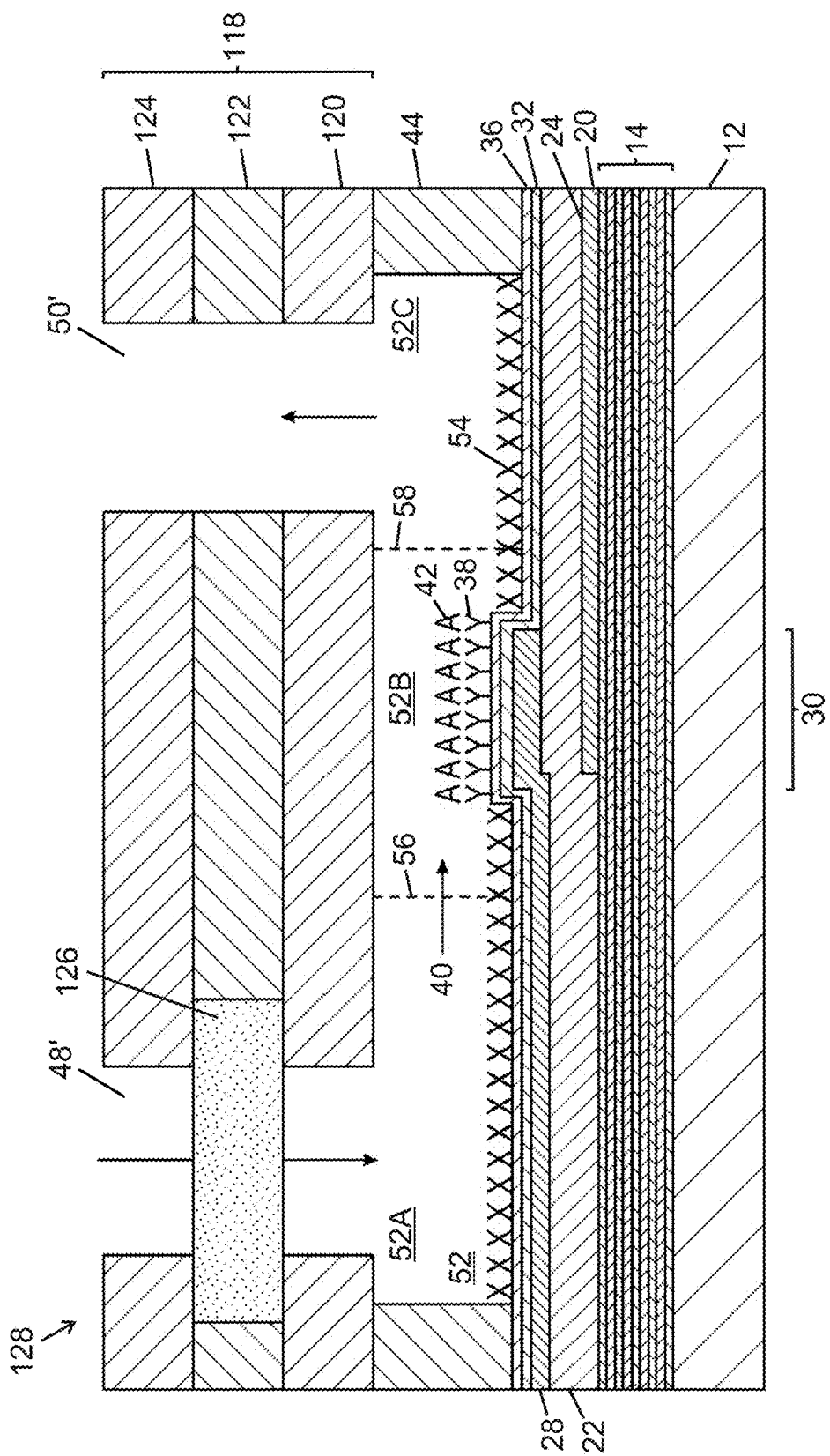
FIG. 9 is a schematic side cross-sectional view of a fluidic device including first and second fluidic ports arranged in fluid communication with a fluidic passage containing an active region of a BAW MEMS resonator structure, with a horizontally arranged porous material associated with a cover structure proximate to the first fluidic port to filter fluid supplied to the first fluidic port, according to one embodiment of the present disclosure.

FIG. 9 is a schematic side cross-sectional view of a fluidic device 128 including first and second fluidic ports 48', 50' arranged in fluid communication with a fluidic passage 52 containing an active region 30 of a BAW MEMS resonator structure, with a horizontally arranged porous material 126 associated with a cover structure 118 to filter fluid supplied to the first fluidic port 48', according to one embodiment of the present disclosure. The fluidic device 128 includes a base structure incorporating a BAW MEMS resonator structure, a wall structure embodied in a wall layer 44 defining lateral boundaries of the fluidic passage 52, and the cover structure 118 that encloses the fluidic passage 52 from above. The base structure includes a substrate 12 overlaid with an acoustic reflector 14, and a piezoelectric material 22 overlying the acoustic reflector 14, wherein a bottom side electrode 20 and a top side electrode 28 are respectively arranged under and over portions of the piezoelectric material 22. A portion of the piezoelectric material 22 arranged between the top side electrode 28 and the bottom side electrode 20 embodies the active region 30 of the BAW resonator structure. The top side electrode 28 and the piezoelectric material 22 are overlaid with a hermeticity layer 32 and a self-assembled monolayer (SAM) 36. Portions of the SAM 36 between the active region 30 and the wall layer 44 are overlaid with a chemical or biological blocking material 54 to prevent localized attachment of functionalization material and/or analyte. A portion of the SAM 36 that is registered with the active region 30 is overlaid with a layer of functionalization (e.g., specific binding) material 38 arranged to bind at least one analyte 42. Walls of the wall layer 44 are laterally displaced from the active region 30 and extend upward from the SAM 36 to define lateral boundaries of the fluidic passage 52 containing the active region 30. More specifically, the active region 30 is provided in a narrowed width intermediate segment 52B disposed between upstream and downstream segments 52A, 52C of the fluidic passage 52. First and second shoulder regions 56, 58 are arranged upstream and downstream, respectively, of inwardly projecting sidewall portions and define transitions (i) between the upstream segment 52A and the intermediate segment 52B, and (ii) between the intermediate segment 52B and the downstream segment 52C, respectively. The cover structure 118 includes a lower layer 120, an intermediate layer 122, and an upper layer 124 each including two holes defined therethrough to form the first and second fluidic ports 48', 50', wherein the porous material 126 is coplanar with the intermediate layer 122 and spans across the first fluidic port 48'. Peripheral edge portions of the porous material 126 (including upper and lower peripheral edges) may be affixed to the upper and lower layers 124, 120 to prevent leakage of fluid past the porous material 126. In certain embodiments, the porous material 126 may be embodied in a porous membrane.

During intended use of the fluidic device 128, a fluid volume 40 may be supplied to the first fluidic port 48' of the cover structure 118 and through the porous material 126 into the upstream segment 52A of the fluidic passage 52. Pore size and other properties of the porous material 126 may be selected to prevent passage of obstruction media (not shown) of a selected type and/or size. From the upstream segment 52A, the fluid volume 40 flows through the intermediate segment 52B over functionalization material 38 overlying the active region 30, and then the fluid volume 40 flows through the downstream segment 52C to the second fluidic port 50' to exit the fluidic passage 52. The analyte 42 contained in one or more lower layers of the fluid volume 40 may bind with functionalization material 38 arranged over the active region 30 in the intermediate segment 52B. Assuming that sufficient analyte 42 is present to bind with functionalization material 38 arranged over the active region 30, when a bulk acoustic wave having a dominant shear component is induced in the active region 30 by supplying an electrical (e.g., alternating current) signal of a desired frequency to the bottom and top side electrodes 20, 28, a change in electroacoustic response (e.g., at least one of an amplitude-magnitude property, a frequency property, or a phase property, such as a shift in resonant frequency) of the BAW resonator structure may be detected to indicate a presence and/or quantity of analyte 42 bound to the functionalization material 38.

In alternative embodiments, one or more porous materials may be associated with the first fluidic port 48' and the second fluidic port 50' of the fluidic device 128, such as to permit the fluidic device 128 to be used in a bidirectional manner and/or provide analyte concentration utility. If one or more porous materials are associated with the first and second fluidic ports 48', 50', then such materials may include the same or different pore sizes and/or other characteristics.

Figure 10:
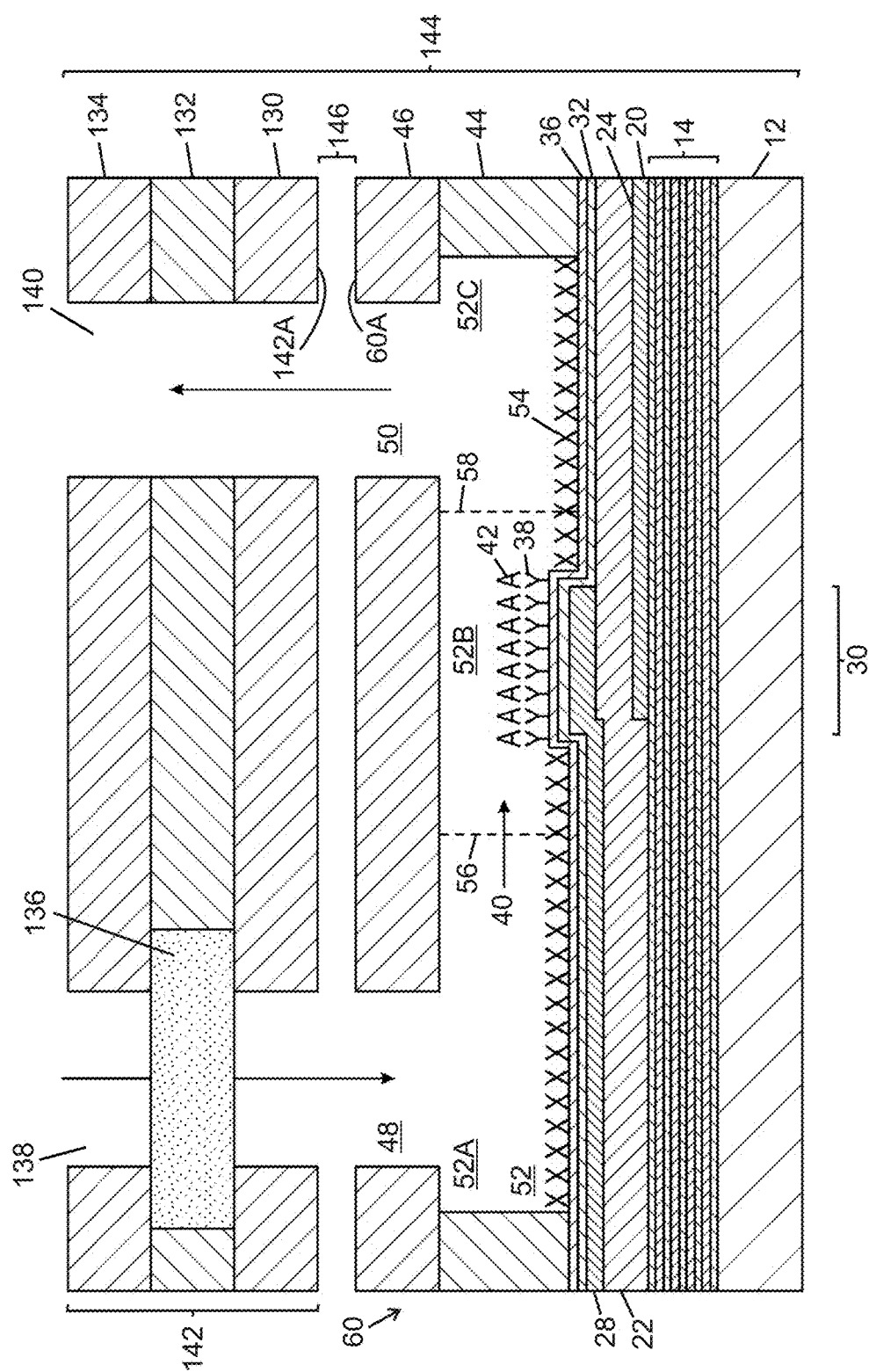
FIG. 10 is a schematic side cross-sectional view of an assembly including the fluidic device of FIGS. 3A and 3B in combination with a filtration cartridge that is distinct from the fluidic device and includes a horizontally arranged porous material arranged upstream of the first fluidic port to filter fluid supplied thereto, according to one embodiment of the present disclosure.

In certain embodiments, a porous material may be arranged upstream of a fluidic port and/or cover structure, such as within a filtration cartridge that is distinct and separable from the cover structure. FIG. 10 is a schematic side cross-sectional view of an assembly 144 including a fluidic device 60 as disclosed in FIGS. 3A and 3B, in combination with a filtration cartridge 142 distinct from the fluidic device 60, with the filtration cartridge 142 including a horizontally arranged porous material 136 arranged upstream of the first fluidic port 48 to filter fluid supplied thereto. Since the fluidic device 60 of FIGS. 3A and 3B has been described in detail hereinabove, such description is hereby incorporated by reference with respect to FIG. 10. The filtration cartridge 142 includes a lower layer 130, an intermediate layer 132, and an upper layer 134 each including two holes defined therethrough to form first and second cartridge ports 138, 140, wherein the porous material 136 is coplanar with the intermediate layer 132 and spans across the first cartridge port 138. Peripheral edge portions of the porous material 136 (including upper and lower peripheral edges) may be affixed to the upper and lower layers 134, 130 to prevent leakage of fluid past the porous material 136. In certain embodiments, the porous material 136 may be embodied in a porous membrane. In certain embodiments, one or more porous materials may also be associated with the second cartridge port 140. As shown in FIG. 10, the fluidic device 60 includes a top surface 60A that may be adjacent to a bottom surface 142A of the filtration cartridge 142. Although a gap 146 between the filtration cartridge 142 and the fluidic device 60 is shown in FIG. 10, it is to be appreciated that in operation, the bottom surface 142A of the filtration cartridge 142 may abut the top surface 60A of the fluidic device 60, or a gasket (not shown) may be arranged therebetween, to enable leak-free fluid communication between the filtration cartridge 142 and the fluidic device 60.

During intended use of the assembly 144, a fluid volume 40 may be supplied to the first cartridge port 138 of the filtration cartridge 142 and through the porous material 136 into the first fluidic port 48 and into the upstream segment 52A of the fluidic passage 52. Pore size and other properties of the porous material 136 may be selected to prevent passage of obstruction media (not shown) of a selected type and/or size. From the upstream segment 52A, the fluid volume 40 flows through the intermediate segment 52B over functionalization material 38 overlying the active region 30, then flows through the downstream segment 52C to the second fluidic port 50, and then flows through the second cartridge port 140 of the filtration cartridge 142. An analyte 42 contained in the fluid volume 40 may bind with functionalization material 38 arranged over the active region 30 in the intermediate segment 52B. Assuming that sufficient analyte 42 is present to bind with functionalization material 38 arranged over the active region 30, when a bulk acoustic wave having a dominant shear component is induced in the active region 30 by supplying an electrical (e.g., alternating current) signal of a desired frequency to the bottom and top side electrodes 20, 28, a change in electroacoustic response (e.g., at least one of an amplitude-magnitude property, a frequency property, or a phase property, such as a shift in resonant frequency) of the BAW resonator structure may be detected to indicate a presence and/or quantity of analyte 42 bound to the functionalization material 38.

One benefit of providing a filtration cartridge that is separable and distinct from a fluidic device containing a BAW resonator structure is that the filtration cartridge may be changed between multiple uses of the fluidic device. In certain embodiments, functionalization material of a fluidic device containing a BAW resonator structure may be regenerated (e.g., stripped with any bound material, and reapplied) between uses, such as disclosed in U.S. patent application Ser. No. 15/334,482 filed Oct. 26, 2016, entitled "Acoustic Resonator Devices and Methods with Noble Metal Layer for Functionalization," with the contents of such application being hereby incorporated by reference herein.

Although various embodiments disclosed herein have included solidly mounted resonator (SMR) type BAW resonator structures, it is to be appreciated that film bulk acoustic resonator (FBAR) structures may be incorporated in fluidic devices in certain embodiments.

Figure 11A:
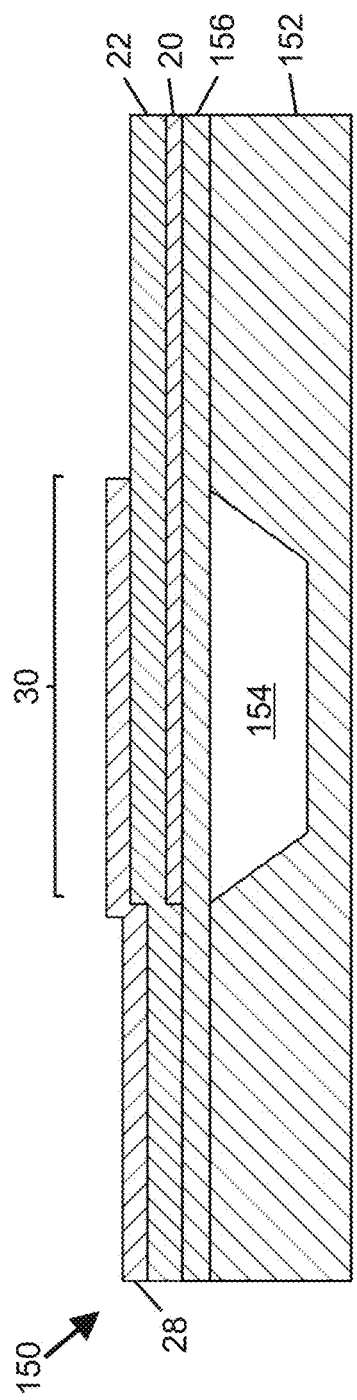
FIG. 11A is a schematic cross-sectional view of a film bulk acoustic wave resonator (FBAR) structure usable in devices according to certain embodiments, with the FBAR structure including an inclined c-axis hexagonal crystal structure piezoelectric material, a substrate defining a cavity optionally covered by a support layer, and an active region registered with the cavity, with a portion of the piezoelectric material arranged between overlapping portions of a top side electrode and a bottom side electrode.

FIG. 11A is a schematic cross-sectional view of a film bulk acoustic wave resonator (FBAR) structure 150 including an active region 30, wherein at least portions of the active region 30 are subject to being overlaid with an interface layer and a self-assembled monolayer (SAM) suitable for receiving a functionalization (e.g., specific binding or non-specific binding) material, according to one embodiment. The FBAR structure 150 includes a substrate 152 (e.g., silicon or another semiconductor material) defining a cavity 154 optionally covered by a support layer 156 (e.g., silicon dioxide). A bottom side electrode 20 is arranged over a portion of the support layer 156, a piezoelectric material 22, preferably embodying inclined c-axis hexagonal crystal structure piezoelectric material (e.g., AlN or ZnO), is arranged over the bottom side electrode 20 and the support layer 156, and a top side electrode 28 is arranged over at least a portion of a top surface of the piezoelectric material 22. A portion of the piezoelectric material 22 arranged between the top side electrode 28 and the bottom side electrode 20 embodies the active region 30 of the FBAR structure 150. The active region 30 is arranged over and registered with the cavity 154 disposed below the support layer 156. The cavity 154 serves to confine acoustic waves induced in the active region 30 by preventing dissipation of acoustic energy into the substrate 152, since acoustic waves do not efficiently propagate across the cavity 154. In this respect, the cavity 154 provides an alternative to the acoustic reflector 14 illustrated in FIGS. 1, 3B, 3D, 4B, 4D, 6B, 9, and 10. Although the cavity 154 shown in FIG. 11A is bounded from below by a thinned portion of the substrate 152, in alternative embodiments at least a portion of the cavity 154 may extend through an entire thickness of the substrate 152. Steps for forming the FBAR structure 150 may include defining the cavity 154 in the substrate 152, filling the cavity 154 with a sacrificial material (not shown) optionally followed by planarization of the sacrificial material, depositing the support layer 156 over the substrate 152 and the sacrificial material, removing the sacrificial material (e.g., by flowing an etchant through vertical openings defined in the substrate 152 or the support layer 156, or lateral edges of the substrate 152), depositing the bottom side electrode 20 over the support layer 156, growing (e.g., via sputtering or other appropriate methods) the piezoelectric material 22, and depositing the top side electrode 28. In certain embodiments, the top side electrode 28, the piezoelectric material 22, and the bottom side electrode 20 in combination may be self-supporting, and the support layer 156 may be omitted and/or removed by etching in the vicinity of the active region 30.

Figure 11B:
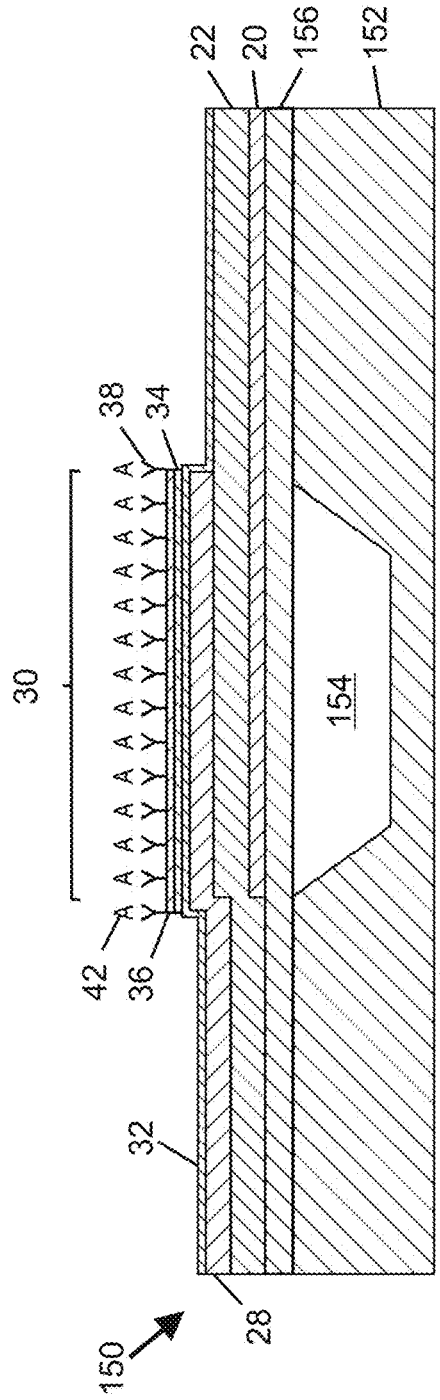
FIG. 11B is a schematic cross-sectional view of the FBAR structure according to FIG. 11A, following addition of a hermeticity layer, an interface layer, a self-assembled monolayer, and a functionalization (e.g., specific binding) material over at least portions of the FBAR structure.

FIG. 11B is a schematic cross-sectional view of the FBAR structure 150 according to FIG. 11A, following addition of a hermeticity layer 32, an interface layer 34, a self-assembled monolayer (SAM) 36, and functionalization material 38 (e.g., specific binding material). The hermeticity layer 32 is arranged over the entire piezoelectric material 22 (as well as the top side electrode 28), whereas the functionalization material 38, the SAM 36, and the interface layer 34 are arranged solely over the active region 30. As shown in FIG. 11B, analyte 42 is bound to the functionalization material 38, such as may occur following exposure of the functionalization material 38 to a medium (e.g., liquid or other fluid) containing the analyte 42, optionally as part of a microfluidic device.

As will be recognized by one skilled in the art upon review of the present disclosure, in certain embodiments, the FBAR structure 150 of FIGS. 11A and 11B may be substituted for the solidly mounted BAW resonator structures disclosed previously herein. In certain embodiments, the FBAR structure 150 of FIG. 11B may be incorporated in a fluidic device including one or more features that provide filtration capability.

Figure 12:
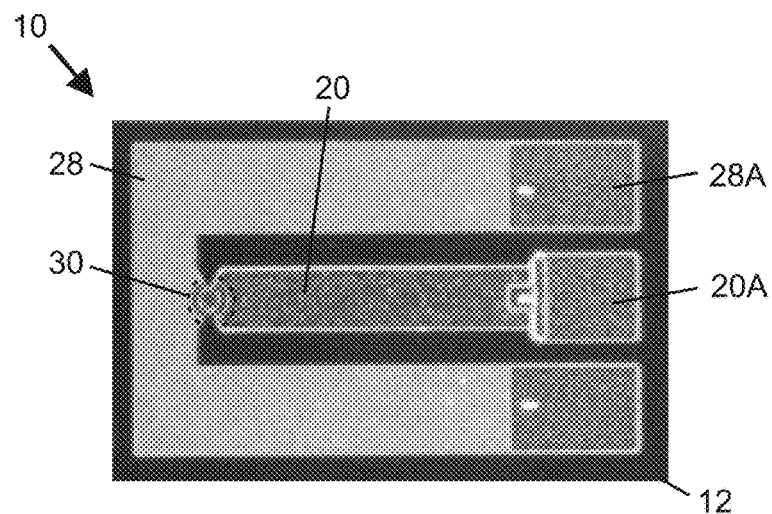
FIG. 12 is a top plan view photograph of a bulk acoustic wave MEMS resonator device suitable for receiving a hermeticity layer, an interface layer, a self-assembled monolayer, and functionalization (e.g. specific binding) material as disclosed herein, and being suitable for inclusion of at least one filtering element as disclosed herein.

FIG. 12 is a top plan view photograph of a bulk acoustic wave MEMS resonator device 10 (consistent with the portion of the resonator device 10 illustrated in FIG. 1) suitable for receiving a hermeticity layer, an interface layer, a self-assembled monolayer, and/or functionalization (e.g., specific binding) material as disclosed herein, and being suitable for inclusion of at least one filtering element as disclosed herein, wherein the MEMS resonator device 10 may serve as a base structure of a fluidic device as disclosed herein. The MEMS resonator device 10 includes a piezoelectric material (not shown) arranged over a substrate 12, a bottom side electrode 20 arranged under a portion of the piezoelectric material, and a top side electrode 28 arranged over a portion of the piezoelectric material, including an active region 30 in which the piezoelectric material is arranged between overlapping portions of the top side electrode 28 and the bottom side electrode 20. Externally accessible contacts 20A, 28A are in electrical communication with the bottom side electrode 20 and the top side electrode 28, respectively. After portions of the resonator device 10 are overlaid with an interface layer, a self-assembled monolayer, and functionalization (e.g., specific binding) material as disclosed herein, the resonator device 10 may be used as a sensor and/or incorporated into a microfluidic device, with wall structures fabricated of photosensitive materials such as SU-8. If desired, multiple resonator devices 10 may be provided in an array on a single substrate 12.

Figure 13:
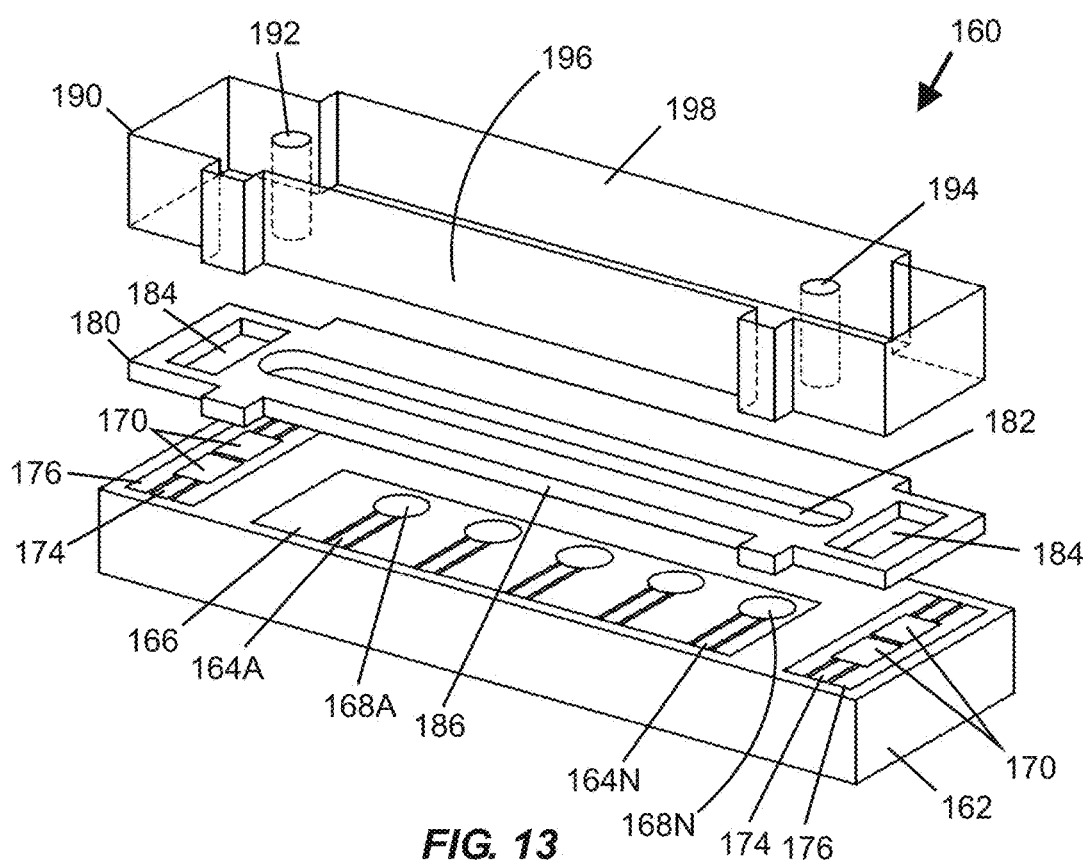
FIG. 13 is a perspective assembly view of a multi-resonator microfluidic device incorporating a base structure including multiple bulk acoustic wave MEMS resonator structures as disclosed herein, a wall structure, and a cover structure.

FIG. 13 is a perspective assembly view of a microfluidic device 160 incorporating a substrate 162 with multiple bulk acoustic wave MEMS resonator devices (forming a base structure), an intermediate wall structure layer 180 defining a central microfluidic channel 182 registered with active regions 168A-168N of the MEMS resonator devices, and a cover structure layer 190 arranged to cover the wall structure layer 180. Although not shown, in certain embodiments the microfluidic device 160 may be modified to include multiple pillars (not shown), may be modified to include a porous material (not shown), or may be used in conjunction with a filtration cartridge (not shown) to provide filtration utility.

Top central portions of the substrate 162, which includes an acoustic reflector (not shown) and a piezoelectric material (not shown), include a top side electrode 166 and bottom side electrodes 164A-164N. Regions in which the foregoing electrodes overlap one another and sandwich the piezoelectric material embody active regions 168A-168N. Any suitable number of active regions 168A-168N may be provided and fluidically arranged in series or parallel, although five active regions are illustrated in FIG. 13. Top peripheral (or top end) portions of the substrate 162 further include reference top side electrodes 176 and reference bottom side electrodes 174 in communication with reference overlap regions 170. Such reference overlap regions 170 are not exposed to fluid, and are present to provide a basis for comparing signals obtained from the active regions 168A-168N exposed to fluid within the central microfluidic channel 182. The substrate 162 is overlaid with the wall structure layer 180, wherein the central microfluidic channel 182 is intended to receive fluid, and defines peripheral chambers 184 arranged to overlie the reference overlap regions 170 in a sealed fashion. The wall structure layer 180 may be formed of any suitable material such as SU-8 negative epoxy resist, other photoresist material, or laser-cut "stencil" layers of thin polymeric materials optionally including one or more self-adhesive surfaces (e.g., adhesive tape), etc. The wall structure layer 180 further includes a lateral inset region 186 that enables lateral portions of the top side electrode 166 and bottom side electrodes 164A-164N to be accessed upon assembly of the microfluidic device 160. The cover structure layer 190 includes a lateral inset region 196 registered with the lateral inset region 186 of the wall structure layer 180, and includes microfluidic ports 192, 194 accessible along a top surface 198 of the cover structure layer 190 and registered with end portions of the central microfluidic channel 182 defined in the wall structure layer 180 to permit fluid (e.g., liquid) to be supplied to the central microfluidic channel 182 over the active regions 168A-168N. Preferably, at least the electrodes 164A-164N, 166 are overlaid with a hermeticity layer, an interface layer, a self-assembled monolayer, and functionalization (e.g., specific binding) material as disclosed herein. In certain embodiments, a driving circuit may be configured to apply alternating current to the electrodes 164A-164N, 166 to cause the piezoelectric material to selectively exhibit a dominant shear response. Microfluidic devices according to other configurations may be provided, as will be recognized by those skilled in the art upon review of the present disclosure.

Technical benefits obtainable with various embodiments of the present disclosure may include reduced blockage of passages of fluidic devices incorporating BAW resonator structures, and/or enhanced ability to detect analytes that are present in low concentration or that exhibit low rates of binding to functionalization material of fluidic devices incorporating bulk acoustic wave resonator structures, including devices suitable for biosensing or biochemical sensing applications.

Those skilled in the art will recognize improvements and modifications to the preferred embodiments of the present disclosure. All such improvements and modifications are considered within the scope of the concepts disclosed herein and the claims that follow.

What is claimed is:

1. A fluidic device comprising:
a base structure comprising: (i) a substrate; and (ii) at least one bulk acoustic wave resonator structure supported by the substrate, the at least one bulk acoustic wave resonator structure including a piezoelectric material, a top side electrode arranged over a portion of the piezoelectric material, and a bottom side electrode arranged below at least a portion of the piezoelectric material, wherein a portion of the piezoelectric material is arranged between the top side electrode and the bottom side electrode to form an active region;
a wall structure arranged over at least a portion of the base structure and defining lateral boundaries of a fluidic passage that is arranged to receive a fluid and contains the active region, wherein the fluidic passage comprises an upstream segment that is upstream of the active region and a downstream segment that is downstream of the active region;
a cover structure arranged over the wall structure and defining an upper boundary of the fluidic passage; and
a plurality of upstream pillars extending into the fluidic passage and being arranged upstream from the active region, wherein each upstream pillar of the plurality of upstream pillars comprises a height that is at least about 50% of an average height of the fluidic passage upstream of the active region, and adjacent upstream pillars of the plurality of upstream pillars are spaced apart from one another by inter-pillar spaces that enable passage of fluid from the upstream segment of the fluidic passage to a portion of the fluidic passage that contains the active region.

2. The fluidic device of claim 1, wherein the plurality of upstream pillars extends upward from the base structure.

3. The fluidic device of claim 1, wherein the plurality of upstream pillars extends downward from the cover structure.

4. The fluidic device of claim 1, wherein each upstream pillar of the plurality of upstream pillars comprises a height that is at least about 90% of the average height of the fluidic passage upstream of the active region.

5. The fluidic device of claim 1, further comprising a plurality of downstream pillars extending into the fluidic passage and being arranged downstream from the active region, wherein each downstream pillar of the plurality of downstream pillars comprises a height that is at least about 50% of an average height of the fluidic passage downstream of the active region, and adjacent downstream pillars of the plurality of downstream pillars are spaced apart from one another by inter-pillar spaces that enable passage of fluid from (i) the portion of the fluidic passage that contains the active region to (ii) the downstream segment of the fluidic passage.

6. The fluidic device of claim 1, wherein the plurality of upstream pillars comprises a first group of upstream pillars including a first average inter-pillar spacing distance, and a second group of upstream pillars including a second average inter-pillar spacing distance, wherein the first average inter-pillar spacing distance is greater than the second average inter-pillar spacing distance, and the first group of upstream pillars is arranged between the first fluidic port and the second group of upstream pillars.

7. The fluidic device of claim 6, further comprising a plurality of downstream pillars extending into the fluidic passage and being arranged downstream from the active region, wherein each downstream pillar of the plurality of downstream pillars comprises a height that is at least about 50% of an average height of the fluidic passage downstream of the active region, and the plurality of downstream pillars includes at least one group of downstream pillars with an inter-pillar spacing distance that is less than the first average inter-pillar spacing distance.

8. The fluidic device of claim 1, wherein the plurality of upstream pillars comprises at least one of a photosensitive material, photoresist, or epoxy.

9. The fluidic device of claim 1, wherein the piezoelectric material comprises a c-axis having an orientation distribution that is predominantly non-parallel to normal of a face of the substrate.

10. The fluidic device of claim 1, wherein:
the fluidic passage further comprises an intermediate segment arranged downstream of the upstream segment;
the plurality of upstream pillars is arranged within the upstream segment;
the intermediate segment contains the active region; and
the upstream segment comprises a greater cross-sectional area than the intermediate segment.

11. The fluidic device of claim 1, further comprising at least one functionalization material arranged over at least a portion of the active region.

12. A method for biological or chemical sensing, the method comprising:
supplying a fluid containing an analyte into the fluidic passage of the fluidic device according to claim 11, wherein said supplying is configured to cause at least a portion of the fluid to pass through the inter-pillar spaces and to cause at least some of the analyte to bind to at least one functionalization material;
inducing a bulk acoustic wave in the active region; and
sensing a change in at least one of an amplitude-magnitude property, a frequency property, or a phase property of the at least one bulk acoustic wave resonator structure to indicate at least one of presence or quantity of target species bound to the at least one functionalization material.

13. A fluidic device comprising:
a base structure comprising: (i) a substrate; and (ii) at least one bulk acoustic wave resonator structure supported by the substrate, the at least one bulk acoustic wave resonator structure including a piezoelectric material, a top side electrode arranged over a portion of the piezoelectric material, and a bottom side electrode arranged below at least a portion of the piezoelectric material, wherein a portion of the piezoelectric material is arranged between the top side electrode and the bottom side electrode to form an active region;
a wall structure arranged over at least a portion of the base structure and defining lateral boundaries of a fluidic passage that is arranged to receive a fluid and contains the active region;
a cover structure arranged over the wall structure and defining an upper boundary of the fluidic passage;
a first fluidic port at least partially defined in at least one of the base structure, the wall structure, or the cover structure and arranged in fluid communication with the fluidic passage upstream of the active region;
a second fluidic port at least partially defined in at least one of the base structure, the wall structure, or the cover structure and arranged in fluid communication with the fluidic passage downstream of the active region; and a plurality of upstream pillars extending into the fluidic passage and being arranged between the first fluidic port and the active region, wherein each upstream pillar of the plurality of upstream pillars comprises a height that is at least about 50% of an average height of the fluidic passage upstream of the active region, and adjacent upstream pillars of the plurality of upstream pillars are spaced apart from one another by inter-pillar spaces that enable passage of fluid between the first fluidic port and a portion of the fluidic passage that contains the active region.

14. The fluidic device of claim 13, wherein the first fluidic port and the second fluidic port are disposed in the cover structure.

\* \* \* \* \*